(12) United States Patent
Morriello et al.

(10) Patent No.: US 9,186,354 B2
(45) Date of Patent: Nov. 17, 2015

(54) PYRROLIDINE DERIVED β3 ADRENERGIC RECEPTOR AGONISTS

(75) Inventors: Gregori J. Morriello, Randolph, NJ (US); Harvey R. Wendt, Medford Lakes, NJ (US); Scott D. Edmondson, Clark, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/811,080

(22) PCT Filed: Jul. 18, 2011

(86) PCT No.: PCT/US2011/044328
§ 371 (c)(1),
(2), (4) Date: Mar. 31, 2014

(87) PCT Pub. No.: WO2012/012314
PCT Pub. Date: Jan. 26, 2012

(65) Prior Publication Data
US 2014/0315912 A1    Oct. 23, 2014

Related U.S. Application Data

(60) Provisional application No. 61/367,048, filed on Jul. 23, 2010.

(51) Int. Cl.
| | | |
|---|---|---|
| C07D 401/14 | (2006.01) |
| A61K 31/435 | (2006.01) |
| C07D 417/14 | (2006.01) |
| C07D 487/04 | (2006.01) |
| C07D 491/107 | (2006.01) |
| A61K 31/4439 | (2006.01) |
| A61K 31/444 | (2006.01) |
| A61K 31/4545 | (2006.01) |
| A61K 31/496 | (2006.01) |
| A61K 31/497 | (2006.01) |
| A61K 31/501 | (2006.01) |
| A61K 31/519 | (2006.01) |
| A61K 45/06 | (2006.01) |
| C07D 237/14 | (2006.01) |
| C07D 413/14 | (2006.01) |

(52) U.S. Cl.
CPC ............ *A61K 31/435* (2013.01); *A61K 31/444* (2013.01); *A61K 31/4439* (2013.01); *A61K 31/4545* (2013.01); *A61K 31/496* (2013.01); *A61K 31/497* (2013.01); *A61K 31/501* (2013.01); *A61K 31/519* (2013.01); *A61K 45/06* (2013.01); *C07D 237/14* (2013.01); *C07D 401/14* (2013.01); *C07D 413/14* (2013.01); *C07D 417/14* (2013.01); *C07D 487/04* (2013.01); *C07D 491/107* (2013.01)

(58) Field of Classification Search
CPC ..................................................... C07D 401/14
USPC ....................................... 546/268.4; 514/340
See application file for complete search history.

(56) References Cited

U.S. PATENT DOCUMENTS

2002/0037907 A1   3/2002   Steffan et al.
2009/0253705 A1   10/2009  Berger et al.

FOREIGN PATENT DOCUMENTS

| WO | WO0232897 | 4/2002 |
| WO | 2009124167 A1 | 10/2009 |
| WO | WO2009/123870 A1 | 10/2009 |
| WO | WO2010129326 | 11/2010 |
| WO | WO2011025774 | 3/2011 |

OTHER PUBLICATIONS

Dorwald, Side Reactions in Organic Synthesis, 2005, Wiley: VCH Weinheim Preface, pp. 1-15 & Chapter 8, pp. 279-308.*
Ahmed et al., Molecular modeling of SWR-0342SA, a B3-selective agonist. with B1-and B3-adrenoceptor:, Life Sciences, 2006, vol. 78, pp. 2019-2023.
EP11810217, Supplementary EP Search Report, Dec. 10, 2013.
Wermuth C.G. et al, Molecular Variations Based on Isosteric Replacements, Practice of Medicinal Chemistry, Jan. 1, 1996, 203-237,—, Academic Press Ltd.

* cited by examiner

*Primary Examiner* — Patricia L Morris
(74) *Attorney, Agent, or Firm* — Patricia A. Shatynski; Catherine D. Fitch

(57) ABSTRACT

The present invention provides compounds of Formula (I), pharmaceutical compositions thereof, and methods of using the same in the treatment or prevention of diseases mediated by the activation of β3-adrenoceptor. (I).

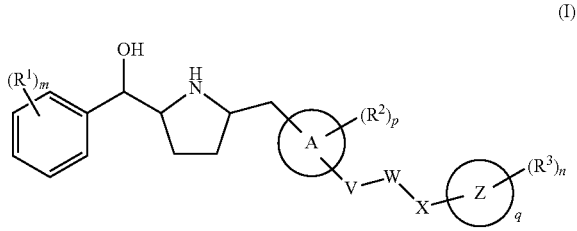

6 Claims, No Drawings

PYRROLIDINE DERIVED β3 ADRENERGIC RECEPTOR AGONISTS

CROSS REFERENCE TO RELATED APPLICATIONS

This application is a U.S. National Phase application under 35 U.S.C. §371 of PCT Application No. PCT/US2011/044328, filed Jul. 18, 2011, which claims priority under 35 U.S.C. §119(e) from U.S. Provisional Application Ser. No. 61/367,048, filed Jul. 23, 2010.

BACKGROUND OF THE INVENTION

The function of the lower urinary tract is to store and periodically release urine. This requires the orchestration of storage and micturition reflexes which involve a variety of afferent and efferent neural pathways, leading to modulation of central and peripheral neuroeffector mechanisms, and resultant coordinated regulation of sympathetic and parasympathetic components of the autonomic nervous system as well as somatic motor pathways. These proximally regulate the contractile state of bladder (detrusor) and urethral smooth muscle, and urethral sphincter striated muscle.

Beta Adrenergic receptors (βAR) are present in detrusor smooth muscle of various species, including human, rat, guinea pig, rabbit, ferret, dog, cat, pig and non-human primate. However, pharmacological studies indicate there are marked species differences in the receptor subtypes mediating relaxation of the isolated detrusor; β1AR predominate in cats and guinea pig, β2AR predominate in rabbit, and β3AR contribute or predominate in dog, rat, ferret, pig, cynomolgus and human detrusor. Expression of βAR subtypes in the human and rat detrusor has been examined by a variety of techniques, and the presence of β3AR was confirmed using in situ hybridization and/or reverse transcription-polymerase chain reaction (RT-PCR). Real time quantitative PCR analyses of β1AR, β2AR and β3AR mRNAs in bladder tissue from patients undergoing radical cystectomy revealed a preponderance of β3AR mRNA (97%, cf 1.5% for β1AR mRNA and 1.4% for β2AR mRNA). Moreover, β3AR mRNA expression was equivalent in control and obstructed human bladders. These data suggest that bladder outlet obstruction does not result in downregulation of βAR, or in alteration of β3AR-mediated detrusor relaxation. β3AR responsiveness also has been compared in bladder strips obtained during cystectomy or enterocystoplasty from patients judged to have normal bladder function, and from patients with detrusor hyporeflexia or hyperreflexia. No differences in the extent or potency of β3AR agonist mediated relaxation were observed, consistent with the concept that the β3AR activation is an effective way of relaxing the detrusor in normal and pathogenic states.

Functional evidence in support of an important role for the β3AR in urine storage emanates from studies in vivo. Following intravenous administration to rats, the rodent selective β3AR agonist CL316243 reduces bladder pressure and in cystomeric studies increases bladder capacity leading to prolongation of micturition interval without increasing residual urine volume.

Overactive bladder is characterized by the symptoms of urinary urgency, with or without urgency urinary incontinence, usually associated with frequency and nocturia. The prevalence of OAB in the United States and Europe has been estimated at 16 to 17% in both women and men over the age of 18 years. Overactive bladder is most often classified as idiopathic, but can also be secondary to neurological condition, bladder outlet obstruction, and other causes. From a pathophysiologic perspective, the overactive bladder symptom complex, especially when associated with urge incontinence, is suggestive of detrusor overactivity. Urgency with or without incontinence has been shown to negatively impact both social and medical well-being, and represents a significant burden in terms of annual direct and indirect healthcare expenditures. Importantly, current medical therapy for urgency (with or without incontinence) is suboptimal, as many patients either do not demonstrate an adequate response to current treatments, and/or are unable to tolerate current treatments (for example, dry mouth associated with anticholinergic therapy). Therefore, there is need for new, well-tolerated therapies that effectively treat urinary frequency, urgency and incontinence, either as monotherapy or in combination with available therapies. Agents that relax bladder smooth muscle, such as β3AR agonists, are expected to be effective for treating such urinary disorders.

SUMMARY OF THE INVENTION

The present invention relates to novel compounds of Formula I or pharmaceutically acceptable salts thereof:

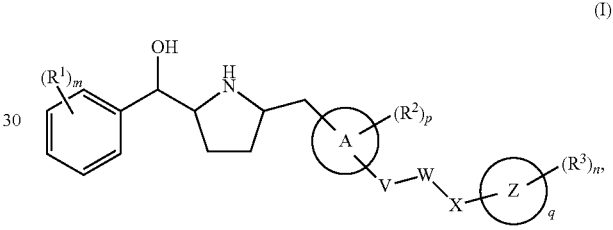

(I)

pharmaceutical compositions containing the compounds disclosed herein, as well as methods for the treatment or prophylaxis of disorders mediated through β3AR.

DESCRIPTION OF THE INVENTION

Described herein are compounds of Formula I or a pharmaceutically acceptable salt thereof:

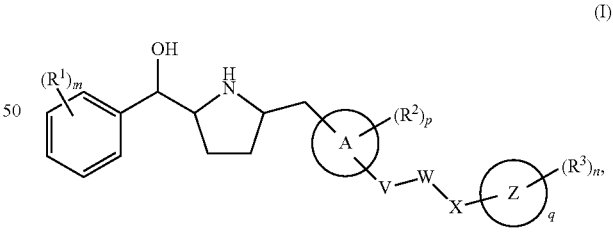

(I)

wherein
m is 0, 1, 2, 3, or 4;
n is 0, 1, 2, 3, or 4;
p is 0, 1, or 2;
q is 0 or 1;
A is selected from the group consisting of pyridyl, pyrimidinyl, pyrazinyl, thiazolyl, thiophenyl;
X is selected from the group consisting of:
   (1) a bond,
   (2) $C_1$-$C_4$ alkanediyl, $C_2$-$C_4$ alkenediyl, and $C_2$-$C_4$ alkynediyl, wherein each of the alkanediyl, alkenediyl and alkynediyl is optionally substituted with 1 to 3 groups independently selected from (a) halogen, and (b) —OR$^a$, and
(3) absent;
V is —NH— and W is a carbonyl group;
or V is a carbonyl group and W is N(R$^4$);
wherein R$^4$ is selected from the group consisting of:
(1) hydrogen, and
(2) C1-C4 alkyl, optionally substituted with 1 to 3 groups independently selected from
(a) hydroxy,
(b) halogen, and
(c) cyano;
or V is a carbonyl group and W is

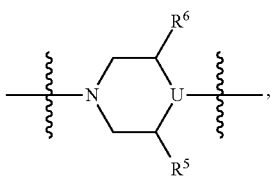

wherein U is CH or N; R$^5$ and R$^6$ are each hydrogen; or R$^5$ and R$^6$ optionally form a direct bond when U is CH;
or V is a carbonyl group and W is

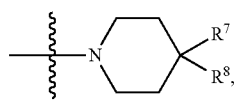

wherein R$^7$ and R$^8$, together with the carbon atom to which they are attached, form a 5- or 6-membered ring containing 0, 1, or 2 hetero atoms independently selected from oxygen, sulfur, and nitrogen; wherein the 5- or 6-membered ring is optionally substituted with 1 to 3 R$^3$ groups;
Z is selected from the group consisting of:
(1) phenyl,
(2) 5 or 6-membered heterocyclic ring with from 1 to 4 heteroatoms independently selected from oxygen, sulfur and nitrogen,
(3) a benzene ring fused to a $C_5$-$C_{10}$ carbocyclic ring,
(4) a $C_5$-$C_8$ carbocyclic ring fused to a 5 or 6-membered heterocyclic ring with from 1 to 4 heteroatoms independently selected from oxygen, sulfur and nitrogen, and
(5) 5 or 6-membered heterocyclic ring with from 1 to 4 heteroatoms independently selected from oxygen, sulfur and nitrogen fused to a 5 or 6-membered heterocyclic ring with from 1 to 4 heteroatoms independently selected from oxygen, sulfur and nitrogen;
each occurrence of R$^1$ is independently selected from the group consisting of:
(1) $C_1$-$C_4$ alkyl optionally substituted with 1 to 3 halogen atoms,
(2) $C_3$-$C_6$ cycloalkyl,
(3) halogen,
(4) nitro,
(5) cyano, and
(6) —CO$_2$R$^a$; and
each occurrence of R$^2$ is independently selected from the group consisting of:
(1) halogen, and
(2) $C_1$-$C_4$ alkyl;

each occurrence of R$^3$ is independently selected from the group consisting of:
(1) halogen,
(2) —OR$^a$,
(3) oxo,
(4) —CO$_2$R$^a$,
(5) —C(O)R$^a$,
(6) —C(O)NR$^a$R$^b$,
(7) —NR$^a$R$^b$,
(8) cyano,
(9) $C_1$-$C_4$ alkyl optionally substituted with 1 to 3 groups independently selected from halogen, —OR$^a$, —CO$_2$R$^a$, C(O)NR$^a$R$^b$ and Z, and
(10) Z optionally substituted with 1-3 groups independently selected from the group consisting of hydroxyl, halogen, oxo, trifluoromethyl, trifluoromethoxy, methyl, ethyl and —CO$_2$H;
each occurrence of R$^a$ is independently selected from the group consisting of:
(1) hydrogen, and
(2) $C_1$-$C_4$ alkyl optionally substituted with 1 to 3 halogen atoms; and
each occurrence of R$^b$ is independently selected from the group consisting of:
(1) hydrogen,
(2) $C_1$-$C_4$ alkyl optionally substituted with 1 to 3 groups independently selected from the group consisting of:
(a) hydroxy, and
(b) halogen,
(3) $C_3$-$C_6$ cycloalkyl, and
(4) phenyl optionally substituted with 1 to 3 groups independently selected from the group consisting of:
(a) halogen,
(b) nitro,
(c) —NR$^a$R$^a$, and
(d) hydroxy.
In one embodiment of Formula (I), compounds disclosed herein have Formula (Ia):

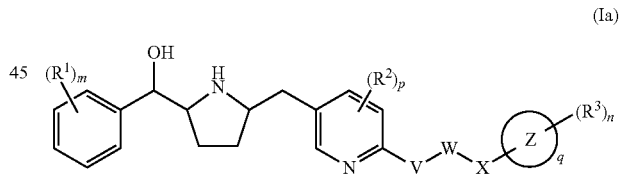

wherein
m is 0, 1, 2, or 3;
n is 0, 1, 2, 3, or 4;
p is 0, 1, or 2;
q is 0 or 1;
X is selected from the group consisting of:
(1) a bond,
(2) $C_1$-$C_4$ alkanediyl, $C_2$-$C_4$ alkenediyl, and $C_2$-$C_4$ alkynediyl, wherein each of the alkanediyl, alkenediyl and alkynediyl is optionally substituted with 1 to 3 groups independently selected from (a) halogen, and (b) —OR$^a$, and
(3) absent;
V is —NH— and W is a carbonyl group;
or V is a carbonyl group and W is N(R$^4$);
wherein R$^4$ is selected from the group consisting of:
(1) hydrogen, and (2) $C_1$-$C_4$ alkyl, optionally substituted with 1 to 3 groups independently selected from
  (a) hydroxy,
  (b) halogen, and
  (c) cyano;
or V is a carbonyl group and W is

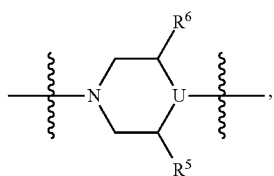

wherein U is CH or N; $R^5$ and $R^6$ are each hydrogen; or $R^5$ and $R^6$ optionally form a direct bond when U is CH;
or V is a carbonyl group and W is

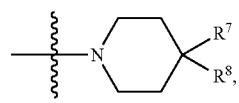

wherein $R^7$ and $R^8$, together with the carbon atom to which they are attached, form a 5- or 6-membered ring containing 0, 1, or 2 hetero atoms independently selected from oxygen, sulfur, and nitrogen; wherein the 5- or 6-membered ring is optionally substituted with 1 to 3 $R^3$ groups;
Z is selected from the group consisting of:
  (1) phenyl,
  (2) 5 or 6-membered heterocyclic ring with from 1 to 4 heteroatoms independently selected from oxygen, sulfur and nitrogen,
  (3) a benzene ring fused to a $C_5$-$C_8$ carbocyclic ring,
  (4) a $C_5$-$C_8$ carbocyclic ring fused to a 5 or 6-membered heterocyclic ring with from 1 to 4 heteroatoms independently selected from oxygen, sulfur and nitrogen, and
  (5) 5 or 6-membered heterocyclic ring with from 1 to 4 heteroatoms independently selected from oxygen, sulfur and nitrogen fused to a 5 or 6-membered heterocyclic ring with from 1 to 4 heteroatoms independently selected from oxygen, sulfur and nitrogen;
each occurrence of $R^1$ is independently selected from the group consisting of:
  (1) $C_1$-$C_4$ alkyl optionally substituted with 1 to 3 halogen atoms,
  (2) $C_3$-$C_6$ cycloalkyl,
  (3) halogen,
  (4) nitro,
  (5) cyano, and
  (6) —$CO_2R^a$; and
each occurrence of $R^2$ is independently selected from the group consisting of:
  (1) halogen, and
  (2) $C_1$-$C_4$ alkyl;
each occurrence of $R^3$ is independently selected from the group consisting of:
  (1) halogen,
  (2) —$OR^a$,
  (3) oxo,
  (4) —$CO_2R^a$,
  (5) —$C(O)R^a$,
  (6) —$C(O)NR^aR^b$,
  (7) —$NR^aR^b$,
  (8) cyano,
  (9) $C_1$-$C_4$ alkyl optionally substituted with 1 to 3 groups independently selected from halogen, —$OR^a$, —$CO_2R^a$, $C(O)NR^aR^b$ and Z, and
  (10) Z optionally substituted with 1-3 groups independently selected from the group consisting of hydroxyl, halogen, oxo, trifluoromethyl, trifluoromethoxy, methyl, ethyl and —$CO_2H$;
each occurrence of $R^a$ is independently selected from the group consisting of:
  (1) hydrogen, and
  (2) $C_1$-$C_4$ alkyl optionally substituted with 1 to 3 halogen atoms; and
each occurrence of $R^b$ is independently selected from the group consisting of:
  (1) hydrogen,
  (2) $C_1$-$C_4$ alkyl optionally substituted with 1 to 3 groups independently selected from the group consisting of:
    (a) hydroxy, and
    (b) halogen,
  (3) $C_3$-$C_6$ cycloalkyl, and
  (4) phenyl optionally substituted with 1 to 3 groups independently selected from the group consisting of:
    (a) halogen,
    (b) nitro,
    (c) —$NR^aR^a$,
    (d) hydroxy.
In one embodiment of Formula (I) or Formula (Ia), each occurrence of $R^1$ is independently selected from the group consisting of:
  (1) $C_1$-$C_4$ alkyl optionally substituted with 1 to 3 halogen atoms, and
  (2) halogen;
each occurrence of $R^2$ is independently selected from the group consisting of:
  (1) halogen, and
  (2) methyl;
each occurrence of $R^3$ is independently selected from the group consisting of:
  (1) halogen,
  (2) —$OR^a$,
  (3) oxo,
  (4) —$CO_2R^a$,
  (5) —$C(O)R^a$,
  (6) —$NR^aR^b$,
  (7) $C_1$-$C_4$ alkyl optionally substituted with 1 to 3 groups independently selected from halogen, —$OR^a$, —$CO_2R^a$, and Z, and
  (8) Z optionally substituted with 1-3 groups independently selected from the group consisting of hydroxyl, halogen, oxo, trifluoromethyl, trifluoromethoxy, methyl, ethyl and —$CO_2H$;
each occurrence of $R^a$ is independently selected from the group consisting of:
  (1) hydrogen, and
  (2) $C_1$-$C_4$ alkyl optionally substituted with 1 to 3 halogen atoms; and
each occurrence of $R^b$ is independently selected from the group consisting of:
  (1) hydrogen, and
  (2) $C_1$-$C_4$ alkyl optionally substituted with 1 to 3 groups independently selected from the group consisting of:
    (a) hydroxy, and
    (b) halogen.
In one subset of the above embodiment, each occurrence of $R^3$ is independently selected from the group consisting of:
  (1) halogen,
  (2) —OH,
  (3) oxo,
  (4) —$CO_2H$, (5) —C(O)H,
(6) —NH$_2$,
(7) methyl optionally substituted with 1 to 3 groups selected from halogen, hydroxyl and Z,
(8) ethyl optionally substituted with 1 to 3 groups selected from halogen, hydroxyl and Z, and
(9) Z optionally substituted with 1-3 groups independently selected from the group consisting of hydroxyl, halogen, oxo, trifluoromethyl, trifluoromethoxy, methyl, ethyl and —CO$_2$H.

In another subset of the above embodiment, each occurrence of R$^3$ is independently selected from the group consisting of:
(1) halogen,
(2) —OH,
(3) oxo,
(4) —CO$_2$H,
(5) methyl optionally substituted with 1 to 3 groups selected from halogen, hydroxyl and Z,
(6) ethyl optionally substituted with 1 to 3 groups selected from halogen, hydroxyl and Z, and
(7) Z optionally substituted with 1-3 groups independently selected from the group consisting of hydroxyl, halogen, oxo, trifluoromethyl, trifluoromethoxy, methyl, ethyl and —CO$_2$H.

In one embodiment of Formula (I) or Formula (Ia), Z is selected from the group consisting of phenyl, oxazolyl, pyridyl, dihydropyridyl, 1,2,3-triazolyl, tetrazolyl, furanyl, tetrahydrofuranyl, piperidinyl, pyrimidinyl, dihydropyrimidinyl, tetrahydropyrimidinyl, pyrazinyl, dihydropyrazinyl, pyridazinyl, dihydropyridazinyl, pyrrolidinyl, imidazolyl, pyrazolyl, 1,2,4-oxadiazolyl, 1,3,4-oxadiazolyl, 1,2,5-oxadiazolyl,

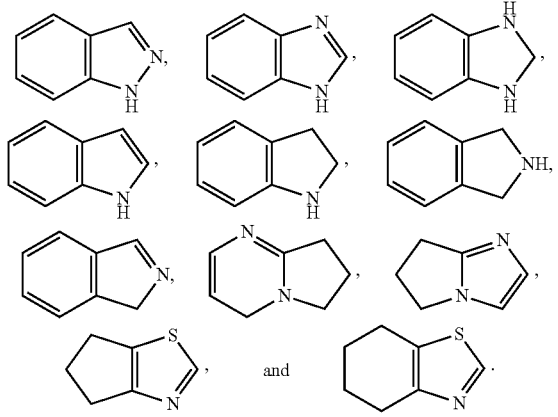

In one subset of the above embodiment, Z is selected from the group consisting of phenyl, pyridyl, dihydropyridyl, 1,2,4-triazolyl, 1,2,3-triazolyl, tetrazolyl, piperidinyl, pyrimidinyl, dihydropyrimidinyl, tetrahydropyrimidinyl, pyrazinyl, dihydropyrazinyl, pyridazinyl, dihydropyridazinyl, pyrrolidinyl, imidazolyl, pyrazolyl, 1,2,4-oxadiazolyl, 1,3,4-oxadiazolyl, 1,2,5-oxadiazolyl,

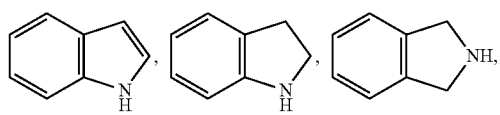

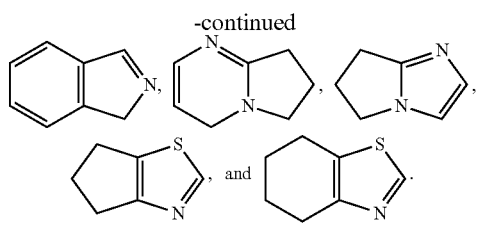

In one embodiment of Formula (I) or Formula (Ia), m is 0, n is 0, 1, 2, or 3, and p is 0.

In one embodiment of Formula (I) or Formula (Ia), V is —NH—; W is a carbonyl group; and X is selected from the group consisting of:
(1) a bond,
(2) methylene, optionally substituted with 1 to 2 halogen atoms, and
(3) ethylene, optionally substituted with 1 to 3 halogen atoms.

In another embodiment of Formula (I) or Formula (Ia), V is a carbonyl group; W is —NH—; and X is selected from the group consisting of:
(1) a bond,
(2) methylene, optionally substituted with 1 to 2 halogen atoms, and
(3) ethylene, optionally substituted with 1 to 3 halogen atoms.

In another embodiment of Formula (I) or Formula (Ia), V is a carbonyl group; W is

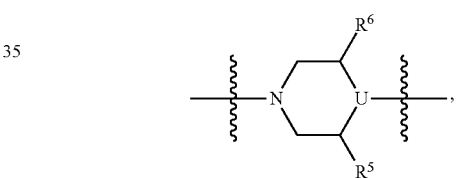

wherein U is CH or N; R$^5$ and R$^6$ are each hydrogen; or R$^5$ and R$^6$ optionally form a direct bond when U is CH; and X is selected from the group consisting of:
(1) a bond,
(2) methylene, optionally substituted with 1 to 2 halogen atoms, and
(3) ethylene, optionally substituted with 1 to 3 halogen atoms.

In another embodiment of Formula (I) Formula (Ia), m is 0; n is 0; p is 0; q is 0; V is a carbonyl group; X is absent; and W is

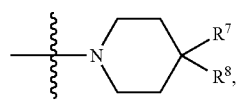

wherein R$^7$ and R$^8$, together with the carbon atom to which they are attached, form a 5- or 6-membered ring containing 0 or 1 hetero atom selected from oxygen and nitrogen; wherein the 5- or 6-membered ring is optionally substituted with 1 to 3 R$^3$ groups.

In one embodiment, compounds disclosed herein have Formula (Ib) or a pharmaceutically acceptable salt thereof:

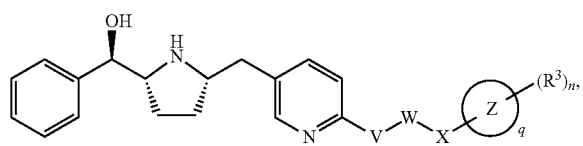

(Ib)

wherein
n is 0, 1, 2 or 3;
q is 0 or 1;
X is selected from the group consisting of:
(1) a bond,
(2) $C_1$-$C_4$ alkanediyl, optionally substituted with 1 to 3 halogen atoms, and
(3) absent; and
V is —NH— and W is a carbonyl group;
or V is a carbonyl group and W is —NH—;
or V is a carbonyl group and W is

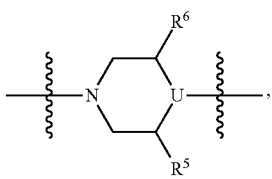

wherein U is CH or N; $R^5$ and $R^6$ are each hydrogen; or $R^5$ and $R^6$ optionally form a direct bond when U is CH;
or V is a carbonyl group and W is

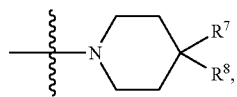

wherein $R^7$ and $R^8$, together with the carbon atom to which they are attached, form a 5- or 6-membered ring containing 0 or 1 hetero atom selected from oxygen and nitrogen; wherein the 5- or 6-membered ring is optionally substituted with 1 to 3 $R^3$ groups;
Z is selected from the group consisting of phenyl, oxazolyl, pyridyl, dihydropyridyl, 1,2,4-triazolyl, 1,2,3-triazolyl, tetrazolyl, furanyl, tetrahydrofuranyl, piperidinyl, pyrimidinyl, dihydropyrimidinyl, tetrahydropyrimidinyl, pyrazinyl, dihydropyrazinyl, pyridazinyl, dihydropyridazinyl, pyrrolidinyl, imidazolyl, pyrazolyl, 1,2,4-oxadiazolyl, 1,3,4-oxadiazolyl, 1,2,5-oxadiazolyl,

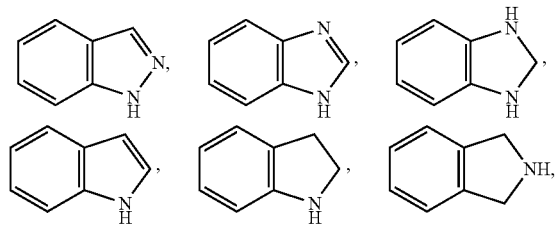

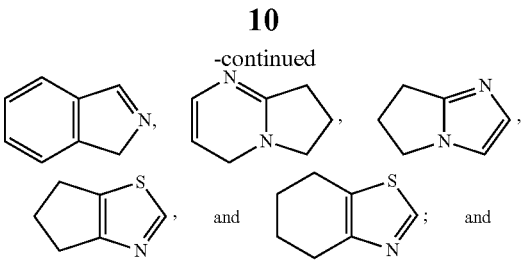

each occurrence of $R^3$ is independently selected from the group consisting of:
(1) halogen,
(2) —OH,
(3) oxo,
(4) —$CO_2H$,
(5) methyl optionally substituted with 1 to 3 groups selected from halogen, hydroxyl and Z,
(6) ethyl optionally substituted with 1 to 3 groups selected from halogen, hydroxyl and Z, and
(7) Z optionally substituted with 1-3 groups independently selected from the group consisting of hydroxyl, halogen, axe, trifluoromethyl, trifluoromethoxy, methyl, ethyl and —$CO_2H$.

In one subset of Formula (Ib), n is 0, 1, 2 or 3; q is 1; X is selected from the group consisting of:
(1) a bond,
(2) methylene, optionally substituted with 1 to 2 halogen atoms, and
(3) ethylene, optionally substituted with 1 to 3 halogen atoms;
V is —NH— and W is a carbonyl group;
or V is a carbonyl group and W is —NH—;
or V is a carbonyl group and W is

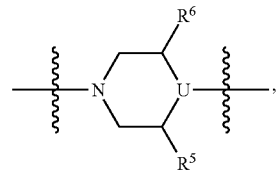

wherein U is CH or N; $R^5$ and $R^6$ are each hydrogen; or $R^5$ and $R^6$ optionally form a direct bond when U is CH;
Z is selected from the group consisting of phenyl, pyridyl, dihydropyridyl, 1,2,4-triazolyl, 1,2,3-triazolyl, tetrazolyl, piperidinyl, pyrimidinyl, dihydropyrimidinyl, tetrahydropyrimidinyl, pyrazinyl, dihydropyrazinyl, pyridazinyl, dihydropyridazinyl, pyrrolidinyl, imidazolyl, pyrazolyl, 1,2,4-oxadiazolyl, 1,3,4-oxadiazolyl, 1,2,5-oxadiazolyl,

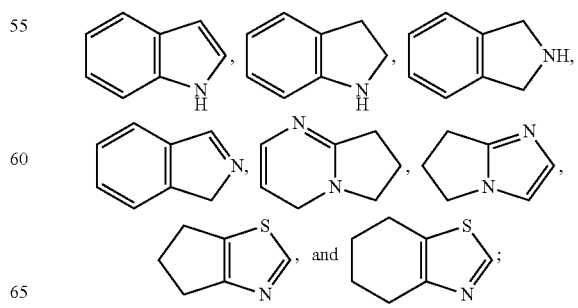

and
each occurrence of $R^3$ is independently selected from the group consisting of:
(1) halogen,
(2) —OH,
(3) oxo,
(4) methyl optionally substituted with 1 to 3 groups selected from halogen, hydroxyl and Z,
(5) ethyl optionally substituted with 1 to 3 groups selected from halogen, hydroxyl and Z, and
(6) Z optionally substituted with 1-3 groups independently selected from the group consisting of hydroxyl, halogen, oxo, trifluoromethyl, trifluoromethoxy, methyl, ethyl and —$CO_2H$.

In one embodiment of the above subset of Formula (Ib), V is —NH—,
W is a carbonyl group, and X is selected from the group consisting of:
(1) a bond,
(2) methylene, and
(3) ethylene.

In another embodiment of the above subset of Formula (Ia), V is a carbonyl group, W is —NH—, and X is selected from the group consisting of:
(1) a bond,
(2) methylene, and
(3) ethylene.

In another embodiment of the above subset of Formula (Ia), V is a carbonyl group, W is selected from the group consisting of

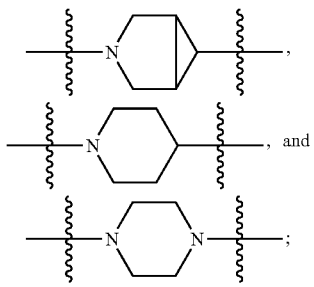

and X is selected from the group consisting of:
(1) a bond,
(2) methylene, and
(3) ethylene.

In another embodiment of the above subset of Formula (Ib), n is 0, 1, 2 or 3; q is 0; V is a carbonyl group; X is absent; and W is

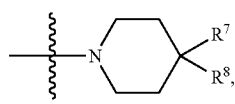

wherein $R^7$ and $R^8$, together with the carbon atom to which they are attached, form a 5-membered ring containing 1 oxygen atom; wherein the 5-membered ring is optionally substituted with 1 to 3 $R^3$ groups selected from:
(1) halogen,
(2) oxo,
(3) methyl, and
(4) ethyl.

In one embodiment of the above subset of Formula (Ib), W is

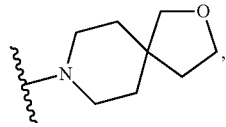 [SMILES: *N1CCC2(CCOC2)CC1]

and wherein the 5-membered ring is optionally substituted with 1 to 2 $R^3$ groups selected from:
(1) halogen, and
(2) oxo.

In one embodiment, compounds disclosed herein have Formula (Ic):

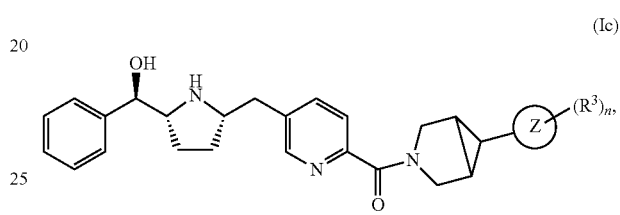

or a pharmaceutically acceptable salt thereof, wherein n, Z, and $R^3$ are as defined above under formula (Ia).

In another embodiment, compounds disclosed herein have Formula (Id):

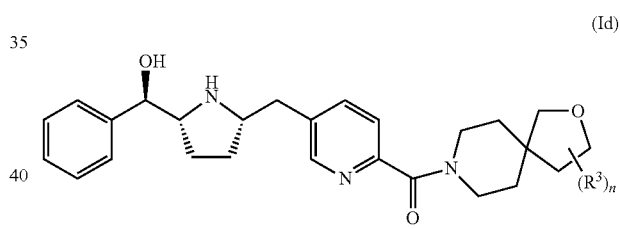

or a pharmaceutically acceptable salt thereof, wherein n and $R^3$ are as defined above under formula (Ia).

For clarity purposes, when "q" of formula (I), (Ia) or (Ib) is 0, then the group Z which is connected to X is absent.

As used herein, the term "alkyl" means both branched- and straight-chain saturated aliphatic hydrocarbon groups having the specified number of carbon atoms. For example, $C_1$-$C_6$ alkyl includes, but is not limited to, methyl (Me), ethyl (Et), n-propyl (Pr), n-butyl (Bu), n-pentyl, n-hexyl, and the isomers thereof such as isopropyl (i-Pr), isobutyl (i-Bu), secbutyl (s-Bu), tert-butyl (t-Bu), isopentyl, sec-pentyl, tert-pentyl, isohexyl and the like.

The term "cycloalkyl" means a monocyclic saturated carbocyclic ring, having the specified number of carbon atoms, e.g., 3, 4, 5 or 6 carbon atoms. Non-limiting examples of $C_3$-$C_6$ cycloalkyl include cyclopropyl, cyclobutyl, cyclopentyl and cyclohexyl.

The term "alkanediyl" means a straight or branched divalent hydrocarbon radical having the specified number of carbon atoms. Non-limiting examples of $C_1$-$C_4$ "alkanediyl" include, but are not limited to, methylene (—$CH_2$—), ethylene (—$CH_2CH_2$—), 1,1-ethanediyl (—$CH(CH_3)$—), 1,2-propanediyl (—$CH(CH_3)CH_2$—), 2-methyl-1,1-propanediyl (—$CH[C(CH_3)_2]$—), 1,4-butanediyl (—CH₂CH₂CH₂CH₂—), 2,3-butanediyl (—CH(CH₃)CH(CH₃)—, and the like. One example of a halogen substituted alkanediyl is —C(CH₃)(F)—.

The term "optionally substituted" means "unsubstituted or substituted," and therefore, the generic structural Formulas described herein encompass compounds containing the specified optional substituent as well as compounds that do not contain the optional substituent. Each variable is independently defined each time it occurs within the generic structural formula definitions.

The terms "halo" or "halogen" are meant to include fluoro, chloro, bromo and iodo, unless otherwise noted.

The terms "carbocycle" or "carbocyclic" refer to saturated, partially unsaturated and aromatic rings having only ring carbon atoms. For example, $C_5$-$C_{10}$ carbocyclic ring include, but are not limited to, cyclopentyl, cyclohexyl, cycloheptyl, cyclooctyl, cyclopentenyl, cyclohexenyl, cyclohexadienyl, and phenyl.

The term "aryl" refers to an aromatic carbocycle.

The terms "heterocycle" or "heterocyclic" refer to saturated, partially unsaturated and aromatic rings having at least one ring heteroatom and at least one ring carbon atom; the heterocycle may be attached to the rest of the molecule via a ring carbon atom or a ring hetero atom, for example, a ring nitrogen atom. The terms "heteroaryl" or "heteroaromatic" refer to an aromatic heterocycle. For example, within the definition for Z, the term "a 5- or 6-membered heterocyclic ring with from 1 to 4 heteroatoms selected from oxygen, sulfur and nitrogen" includes, but is not limited to, pyrrolyl, thienyl, (uranyl, imidazolyl, pyrazolyl, oxazolyl, isoxazolyl, thiazolyl, isothiazolyl, triazolyl, tetrazolyl, oxadiazolyl, thiadiazolyl, pyrrolidinyl, tetrahydrofuranyl, pyridinyl, dihydropyridinyl, tetrahydropyridinyl, pyrimidinyl, dihydropyrimidinyl, tetrahydropyrimidinyl, pyrazinyl, dihydropyrazinyl, tetrahydropyrazinyl, pyridazinyl, dihydropyridazinyl, tetrahydropyridazinyl, piperidinyl, piperazinyl, morpholinyl, pyranyl, dihydropyranyl, tetrahydropyranyl, and the like.

Within the definition for Z, the term "a benzene ring fused to a $C_5$-$C_{10}$ carbocyclic ring" includes, but is not limited to, naphthyl, dihydronaphthyl, tetrahydronaphthyl, indanyl, indenyl, benzocycloheptene, tetrahydrobenzocyloheptene, and the like. In one embodiment, a benzene ring is fused to a $C_5$-$C_6$ carbocyclic ring. Such fused ring may be attached to the rest of the molecule via a carbon atom on either ring.

Within the definition for Z, the term "a 5- or 6-membered heterocyclic ring with from 1 to 4 heteroatoms independently selected from oxygen, sulfur and nitrogen fused to a 5- or 6-membered heterocyclic ring with from 1 to 4 heteroatoms independently selected from oxygen, sulfur and nitrogen" includes, but is not limited to, naphthyridinyl, dihydronaphthyridinyl, tetrahydronaphthyridinyl, imidazopyridinyl, pteridinyl, purinyl, quinolizinyl, indolizinyl, tetrahydroquinolizinyl, and tetrahydroindolizinyl. In one embodiment, Z is selected from the group consisting of:

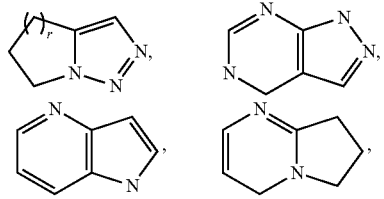

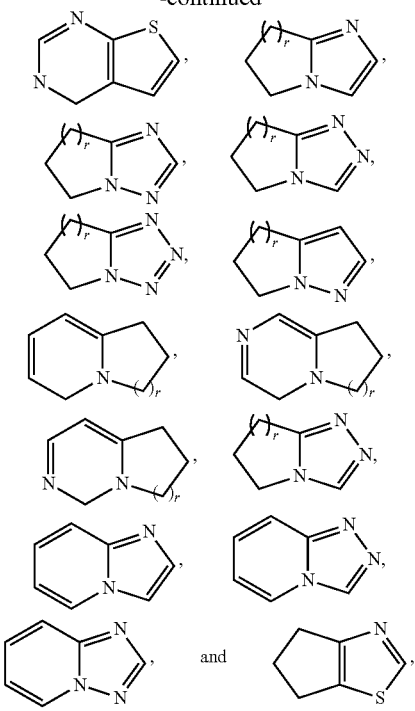

wherein r is 1 or 2. Such fused ring may be attached to the rest of the molecule via a carbon atom or a nitrogen atom on either ring.

To avoid any doubt, the term "a 5- or 6-membered heterocyclic ring with from 1 to 4 heteroatoms independently selected from oxygen, sulfur and nitrogen fused to a 5- or 6-membered heterocyclic ring with from 1 to 4 heteroatoms independently selected from oxygen, sulfur and nitrogen" as used herein includes compounds having only one nitrogen as the sole heteroatom when the nitrogen is located at the bridgehead.

Within the definition for Z, the term "a $C_5$-$C_{10}$ carbocyclic ring fused to a 5- or 6-membered heterocyclic ring with from 1 to 4 heteroatoms independently selected from oxygen, sulfur and nitrogen" includes, but is not limited to, indolyl, isoindolyl, benzofuranyl, benzothienyl, benzimidazolyl, benzotriazolyl, benzoxazolyl, benzisoxazolyl, benzthiazolyl, benzisothiazolyl, quinolinyl, isoquinolinyl, quinoxalinyl, quinazolinyl, cinnolinyl, indazolyl, tetrahydroquinolinyl, tetrahydroindazolyl, dihydroindazolyl, chromenyl, chromanyl benztriazolyl,

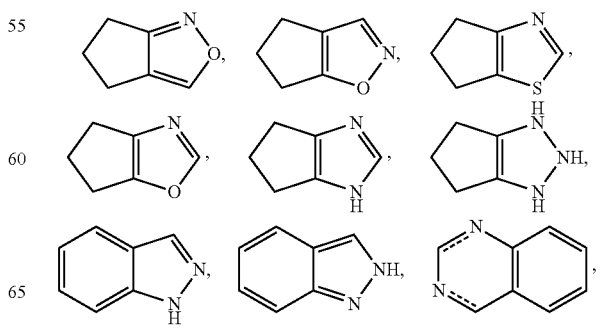

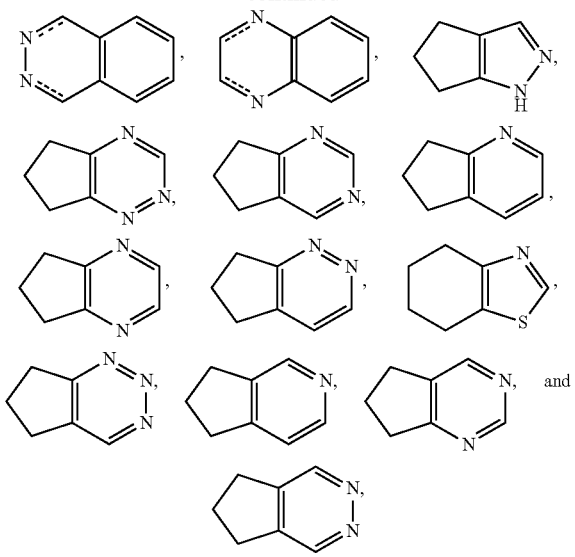

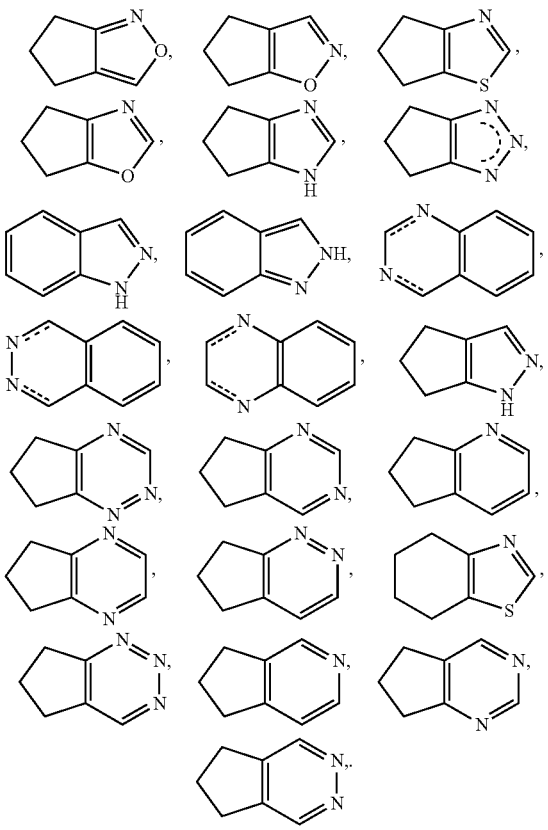

where the dash bond "═" means a single or double bond while conforming to the valency rule for the ring atoms. Such fused ring may be attached to the rest of the molecule via a carbon atom on either ring or a nitrogen atom on the heterocyclic ring.

For the terms $(R^1)_m$, $(R^2)_p$, and $(R^3)_n$, as well as other similar notations, when m, n or p is 0, then $R^1$, $R^2$ or $R^3$ is hydrogen; when m, n or p is greater than 1, then each occurrence of $R^1$, $R^2$ or $R^3$ is independently selected from other occurrences of $R^1$, $R^2$ or $R^3$, respectively. For example, when n is 2, the two $R^3$ substituents can be the same or different.

In one embodiment, Z is a 5- or 6-membered heterocyclic ring with from 1 to 4 heteroatoms independently selected from oxygen, sulfur and nitrogen. In one subset Z is a 5-membered heterocycle having one nitrogen atom and 0 to 2 additional heteroatoms independently selected from N, O and S. In another subset Z is a 6-membered heterocycle having 1, 2 or 3 nitrogen atoms, or 1 nitrogen atom and an oxygen or sulfur atom. In yet another subset, Z is selected from the group consisting of thiazolyl, oxazolyl, pyridyl, dihydropyridyl, triazolyl (including 1,2,4-triazolyl and 1,2,3-triazolyl), tetrazolyl, pyrimidinyl, dihydropyrimidinyl, tetrahydropyrimidinyl, pyrazinyl, dihydropyrazinyl, pyridazinyl, dihydropyridazinyl, pyrrolidinyl, imidazolyl, pyrazolyl, and oxadiazolyl (including 1,2,4-oxadiazolyl and 1,2,5-oxadiazolyl).

In another embodiment, Z is a $C_5$-$C_8$ carbocyclic ring fused to a 5- or 6-membered heterocyclic ring with from 1 to 4 heteroatoms independently selected from oxygen, sulfur and nitrogen. In one subset the carbocyclic ring is a $C_5$-$C_6$ carbocyclic ring. In another subset the heterocycle is either a 5-membered heterocycle having one nitrogen atom and 0 to 3 additional heteroatoms independently selected from N, O and S, or a 6-membered heterocycle having 1, 2 or 3 nitrogen atoms, or 1 nitrogen atom and an oxygen or sulfur atom, and the carbocycle has 5 or 6 carbon atoms. In yet another subset Z is selected from the group consisting of: indolyl, benzimidazolyl, benzthiazolyl, quinolinyl, isoquinolinyl, tetrahydroquinolinyl, tetrahydroisoquinolinyl, chromenyl, benztriazolyl, In another embodiment, Z is a 5- or 6-membered heterocyclic ring with from 1 to 4 heteroatoms independently selected from oxygen, sulfur and nitrogen fused to a 5- or 6-membered heterocyclic ring with from 1 to 4 heteroatoms independently selected from oxygen, sulfur and nitrogen. In one subset the fused ring has 2 to 5 heteroatoms, at least one of which is nitrogen. In another subset the fused ring has 2 to 4 nitrogen atoms and no other heteroatoms. In yet another subset the fused ring has one oxygen or sulfur atom, and 1 to 3 nitrogen atoms. In yet another subset, Z is selected from the group consisting of

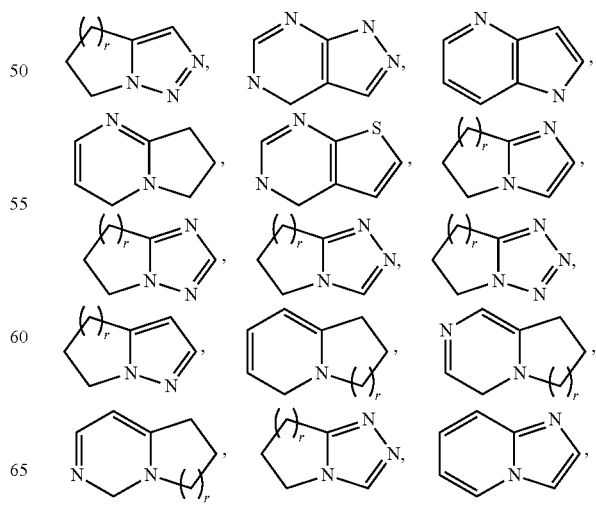

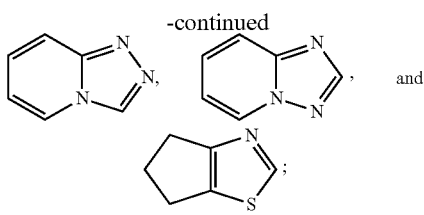

and wherein r is 1 or 2.

In one embodiment, compounds described herein are as described in the Examples below.

Optical Isomers-Diastereomers-Geometric Isomers-Tautomers

Compounds described herein may contain an asymmetric center and may thus exist as enantiomers. Where the compounds according to the invention possess two or more asymmetric centers, they may additionally exist as diastereomers. When bonds to the chiral carbon are depicted as straight lines in the formulas of the invention, it is understood that both the (R) and (S) configurations of the chiral carbon, and hence both enantiomers and mixtures thereof, are embraced within the formulas. The present invention includes all such possible stereoisomers as substantially pure resolved enantiomers, racemic mixtures thereof, as well as mixtures of diastereomers. The above Formulas I and Ia are shown without a definitive stereochemistry at certain positions. The present invention includes all stereoisomers of Formulas I and Ia and pharmaceutically acceptable salts thereof.

Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound described herein may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl —$CH_2C(O)$— groups (keto forms) may undergo tautomerism to form hydroxyl $CH=C(OH)$— groups (enol forms). Both keto and enol forms, individually as well as mixtures thereof, are included within the scope of the present invention.

Isotopes

In the compounds described herein, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds described herein. For example, different isotopic forms of hydrogen (H) include protium ($^1H$) and deuterium ($^2H$). Protium is the predominant hydrogen isotope found in nature Enriching for deuterium may afford certain therapeutic advantages, such as increasing in vivo half-life or reducing dosage requirements, or may provide a compound useful as a standard for characterization of biological samples. Isotopically-enriched compounds described herein can be prepared without undue experimentation by conventional techniques well known to those skilled in the art or by processes analogous to those described in the Schemes and Examples herein using appropriate isotopically-enriched reagents and/or intermediates.

Salts

The term "pharmaceutically acceptable salts" refers to salts prepared from pharmaceutically acceptable non-toxic bases or acids. When a compound described herein is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glutamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When a compound described herein is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

Solvates

The present invention includes within its scope solvates of compounds disclosed herein. As used herein, the term "solvate" refers to a complex of variable stoichiometry formed by a solute (e.g., a compound of Formula I, Ia, Ib, Ic or Id) or a pharmaceutically acceptable salt thereof and a solvent that does not interfere with the biological activity of the solute. Examples of solvents include, but are not limited to water, ethanol, and acetic acid. When the solvent is water, the solvate is known as hydrate; hydrates include, but are not limited to, hemi-, mono, sesqui-, di- and trihydrates.

Prodrugs

The present invention includes within its scope the use prodrugs of the compounds described herein. In general, such prodrugs will be functional derivatives of the compounds of this invention which are readily convertible in vivo into the required compound. Thus, in the methods of treatment of the present invention, the term "administering" shall encompass the treatment of the various conditions described with a compound described herein or with a compound which may not be a compound described herein, but which converts to a compound described herein in vivo after administration to the patient. Conventional procedures for the selection and preparation of suitable prodrug derivatives are described, for example, in "Design of Prodrugs," ed. H. Bundgaard, Elsevier, 1985.

Utilities

Compounds described herein are potent agonists of the β3-adrenoceptor, and as such are useful in treating or preventing diseases, disorders or conditions mediated by the activation of β3-adrenoceptor. Thus one aspect of the present invention provides a method for the treatment, control or prevention of such diseases, disorders, or conditions in a mammal which comprises administering to such mammal a therapeutically effective amount of a compound described herein. The term "mammal" includes human and non-human animals such as dogs and cats and the like. The diseases, disorders or conditions for which compounds of the present invention are useful in treating or preventing include, but are not limited to, (1) overactive bladder, (2) urinary incontinence, (3) urge urinary incontinence, (4) urinary urgency, (5) diabetes mellitus, (6) hyperglycemia, (7) obesity, (8) hyperlipidemia, (9) hypertriglyceridemia, (10) hypercholesterolemia, (11) atherosclerosis of coronary, cerebrovascular and peripheral arteries, (12) gastrointestinal disorders including peptide ulcer, esophagitis, gastritis and duodenitis, (including that induced by *H. pylori*), intestinal ulcerations (including inflammatory bowel disease, ulcerative colitis, Crohn's disease and proctitis) and gastrointestinal ulcerations, (13) neurogenic inflammation of airways, including cough, asthma, (14) depression, (15) prostate diseases such as benign prostate hyperplasia, (16) irritable bowel syndrome and other disorders needing decreased gut motility, (17) diabetic retinopathy, (18) preterm labor, and (19)-elevated intraocular pressure and glaucoma.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds described herein are administered orally.

The effective dosage of active ingredient employed may vary depending on the particular compound employed, the mode of administration, the condition being treated and the severity of the condition being treated. Such dosage may be ascertained readily by a person skilled in the art.

When treating overactive bladder (OAB) in conjunction with other anti-OAB agents, or alone, generally satisfactory results are obtained when the compounds of the present invention are administered at a daily dosage of from 0.01 mg to about 100 mg per kg of animal body weight, preferably given in a single dose or in divided doses two to six times a day, or in sustained release form. In the case of a 70 kg adult human, the total daily dose will generally be from about 0.7 mg to about 3500 mg, or more specifically, from about 0.7 mg to about 2000 mg. This dosage regimen may be adjusted to provide the optimal therapeutic response.

When treating obesity, in conjunction with diabetes and/or hyperglycemia, or alone, generally satisfactory results are obtained when the compounds of the present invention are administered at a daily dosage of from 0.01 mg to about 100 mg per kg of animal body weight, preferably given in a single dose or in divided doses two to six times a day, or in sustained release form. In the case of a 70 kg adult human, the total daily dose will generally be from about 0.7 mg to about 3500 mg. This dosage regimen may be adjusted to provide the optimal therapeutic response.

When treating diabetes mellitus and/or hyperglycemia, as well as other diseases or disorders for which compounds described herein are useful, generally satisfactory results are obtained when the compounds of the present invention are administered at a daily dosage of from about 0.001 mg to about 100 mg per kg of animal body weight, preferably given in a single dose or in divided doses two to six times a day, or in sustained release form. In the case of a 70 kg adult human, the total daily dose will generally be from about 0.07 mg to about 350 mg. This dosage regimen may be adjusted to provide the optimal therapeutic response.

In one embodiment, a compound of the present invention is used in the manufacture of a medicament for the treatment or prevention of a disease or disorder mediated by the activation of β3-adrenoceptor.

Another aspect of the present invention provides pharmaceutical compositions which comprises a compound described herein and a pharmaceutically acceptable carrier. The pharmaceutical compositions of the present invention comprise a compound described herein as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, intravesical, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds described herein can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds described herein may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Compounds described herein may be used in combination with other drugs that are used in the treatment prevention suppression or amelioration of the diseases or conditions for which compounds described herein are useful. Such other drugs may be administered, by a route and in an amount commonly used therefor, contemporaneously or sequentially with a compound described herein. When a compound described herein is used contemporaneously with one or more other drugs, a pharmaceutical unit dosage form containing such other drugs in addition to the compound described herein is preferred. Accordingly, the pharmaceutical compositions of the present invention include those that also contain one or more other active ingredients, in addition to a compound described herein. Examples of other active ingredients that may be combined with a compound described herein, either administered separately or in the same pharmaceutical compositions, include, but are not limited to:

(a) overactive bladder medicines including (i) muscarinic receptor antagonists (e.g. tolterodine, oxybutynin including S-oxybutynin, hyoscyamine, propantheline, propiverine, trospium including trospium chloride, solifenacin, darifenacin, imidafenacin, fesoterodine, temiverine, SVT-40776, 202405 by GlaxoSmithKline, TD6301, RBX9841, DDP200, PLD179, and other anticholinergics. See, for example, U.S. Pat. No. 5,382,600; U.S. Pat. No. 3,176,019; U.S. Pat. No. 3,480,626; U.S. Pat. No. 4,564,621; U.S. Pat. No. 5,096,890; U.S. Pat. No. 6,017,927; U.S. Pat. No. 6,174,896; U.S. Pat. No. 5,036,098; U.S. Pat. No. 5,932,607; U.S. Pat. No. 6,713,464; U.S. Pat. No. 6,858,650; and DD 106643. See also, U.S. Pat. No. 6,103,747; U.S. Pat. No. 6,630,462; U.S. Pat. No. 6,770,295; U.S. Pat. No. 6,911,217; U.S. Pat. No. 5,164,190; U.S. Pat. No. 5,601,839; U.S. Pat. No. 5,834,010; U.S. Pat. No. 6,743,441; WO2002000652; WO200400414853. As will be appreciated by those of skill in the art, these drugs may be administered orally or topically in standard or extended release forms, such as extended release tolterodine, extended releases oxybutynin and transdermal oxybutynin), (ii) NK-1 or NK-2 antagonists (e.g. aprepitant, cizolirtine, compounds disclosed in WO2005/073191, WO2005/032464, and other reported NK-1 antagonists), (iii) alpha adrenergic receptor antagonists (e.g. alfuzosin, doxazosin, prazosin, tamsulosin, terazosin, and others), (iv) potassium channel openers (e.g. cromakalim, pinacidil, and others), (v) vanilloids and other afferent-nerve modulators—agonists and antagonists (e.g. capsaicin, resiniferatoxin, and others), (vi) dopamine D1 receptor agonists (e.g. pergolinde), (vii) serotonergic and/or norepinephrine reuptake inhibitors (e.g. duloxetine), (viii) neuromuscular junction inhibition of acetylcholine release (e.g. botulinum toxin), (ix) calcium channel blockers (e.g. diltiazem, nifedipine, verapamil, and others), (x) inhibitors of prostaglandin synthesis (e.g. flurbiprofen), (xi) gamma aminobutyric acid receptor antagonists (e.g. baclofen), (xii) vaginal estrogen preparations (xiii) selective norepinephrine reuptake inhibitors, (xiv) 5-HT2C agonists, (xv) voltage gated sodium channel blocker, (xvi) P2X purinergic receptor antagonists (e.g. P2X1 or P2X3 antagonists), (xvii) PAR2 inhibitors, (xviii) phosphodiesterase inhibitors (e.g. PDE1, PDE4, and PDE5 inhibitors); and (xix) ATP sensitive potassium channel openers.

(b) insulin sensitizers including (i) PPARγ agonists such as the glitazones (e.g. troglitazone, pioglitazone, englitazone, MCC-555, BRL49653 and the like), and compounds disclosed in WO97/27857, 97/28115, 97/28137 and 97/27847; (ii) biguanides such as metformin and phenformin;

(c) insulin or insulin mimetics;

(d) sulfonylureas such as tolbutamide and glipizide;

(e) α-glucosidase inhibitors (such as acarbose), (f) cholesterol lowering agents such as (i) HMG-CoA reductase inhibitors (lovastatin, simvastatin and pravastatin, fluvastatin, atorvastatin, and other statins), (ii) sequestrants (cholestyramine, colestipol and a dialkylaminoalkyl derivatives of a cross-linked dextran), (ii) nicotinyl alcohol nicotinic acid or a salt thereof, (iii) proliferator-activater receptor a agonists such as fenofibric acid derivatives (gemfibrozil, clofibrat, fenofibrate and benzafibrate), (iv) inhibitors of cholesterol absorption for example beta-sitosterol and ezetimibe, and (acyl CoA:cholesterol acyltransferase) inhibitors for example melinamide, (v) probucol, (vi) vitamin E, and (vii) thyromimetics;

(g) PPARδ agonists such as those disclosed in WO97/28149;

(h) antiobesity compounds such as fenfluramine, dexfenfluramine, phentermine, sibutramine, orlistat, and other $\beta_3$ adrenergic receptor agonists;

(i) feeding behavior modifying agents such as neuropeptide Y antagonists (e.g. neuropeptide Y5) such as those disclosed in WO 97/19682, WO 97/20820, WO-97/20821, WO 97/20822 and WO 97/20823;

(j) PPARα agonists such as described in WO 97/36579 by Glaxo;

(k) PPARγ antagonists as described in WO97/10813; and (l) serotonin reuptake inhibitors such as fluoxetine and sertraline.

In one embodiment, a compound of the present invention and a second active agent as described above are used in the manufacture of a medicament for the treatment or prevention of a disease or disorder mediated by the activation of β3-adrenoceptor.

The compounds of disclosed herein can be prepared according to the procedures of the following Schemes and Examples using appropriate materials, and are further exemplified by the following specific examples. Moreover, by utilizing the procedures described herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogen carbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electron-spray ion-mass spectroscopy.

A variety of chromatographic techniques may be employed in the preparation of the compounds. These techniques include, but are not limited to: High Performance Liquid Chromatography (HPLC) including normal phase, reversed phase, and chiral phase HPLC; Medium Pressure Liquid Chromatography (MPLC), Super Critical Fluid Chromatography; preparative Thin Layer Chromatography (prep TLC); flash chromatography with silica gel or reversed-phase silica gel; ion-exchange chromatography; and radial chromatography. All temperatures are degrees Celsius unless otherwise noted.

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT and HOAT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. MOZ and BOC are commonly used protecting groups in organic synthesis, and their removal conditions are known to those skilled in the art. For example, MOZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of MOZ groups can also be achieved by treatment with a solution of trifluoroacetic acid, hydrochloric acid or hydrogen chloride gas, in a solvent such as dichloromethane, methanol, or ethyl acetate. Removal of BOC protecting groups is carried out with a strong acid, such as trifluoroacetic acid, hydrochloric acid, or hydrogen chloride gas, in a solvent such as dichloromethane, methanol, or ethyl acetate.

Throughout the application, the following terms have the indicated meanings unless noted otherwise:

| Term | Meaning |
| --- | --- |
| Ac | Acyl ($CH_3C(O)$—) |
| BOC (Boc) | t-Butyloxycarbonyl |
| BOP | Benzotriazol-1-yloxytris(dimethylamino)phosphonium hexafluorophosphate |
| ° C. | Degree Celsius |
| Calc. or calc'd | Calculated |
| Celite | Celite ™ diatomaceous earth |
| DCC | Dicyclohexylcarbodiimide |
| DCM | Dichloromethane |
| DIEA | N,N-diisopropyl-ethylamine |
| DMF | N,N-dimethylformamide |
| EDC | 1-Ethyl-3-(3-dimethylaminopropyl) carbodiimide |
| Eq. or equiv. | Equivalent(s) |
| ES-MS and ESI-MS | Electron spray ion-mass spectroscopy |
| Et | Ethyl |
| EtOAc | Ethyl acetate |
| g | Gram(s) |
| h or hr | Hour(s) |
| HATU | O-(7-azabenzotriazol-1-yl)-N, N, N, N'-tetramethyluronium hexafluorophosphate |
| HCl | Hydrogen chloride |
| HOAc | Acetic acid |
| HOAT | 1-Hydroxy-7-azabenzotriazole |
| HOBT | 1-Hydroxybenzotriazole |
| HPLC | High performance liquid chromatography |
| IPA | Isopropyl alcohol |
| kg | Kilogram(s) |
| LC/MS or LC-MASS | Liquid chromatography mass spectrum |
| L | Liter(s) |
| LDA | Lithium diisopropylamide |
| LiOH | Lithium hydroxide |
| LiHMDS | Lithium bis(trimethylsilyl)amide |
| M | Molar(s) |
| Me | Methyl |
| MeOH | Methanol |
| MF | Molecular formula |
| min | Minute(s) |
| mg | Milligram(s) |
| mL | Milliliter(s) |
| mmol | Millimole(s) |
| MOZ (Moz) | p-Methoxybenzyloxycarbonyl |
| MP | Melting point |
| MS | Mass spectrum |
| NaH | Sodium hydride |
| nM | Nanomolar |
| OTf | Trifluoromethanesulfonyl |
| 10% Pd/C | Palladium, 10 weight percent on activated carbon |
| Ph | Phenyl |
| Prep. | Preparative |
| Ref. | Reference |
| r.t. or rt or RT | RT |
| Sat. | Saturated |
| SCF $CO_2$ S | Super critical fluid carbon dioxide |
| TBAF | Tetrabutylammonium fluoride |
| TBAI | Tetrabutylammonium iodide |
| TBDPS | Tert-butyl diphenylsilyl |
| TBS, TBDMS | Tert-butyl dimethylsilyl |
| TEA or $Et_3N$ | Triethylamine |
| Tf | Triflate or trifluoromethanesulfonate |
| TFA | Trifluoroacetic acid |
| THF | Tetrahydrofuran |
| TLC | Thin-layer chromatography |
| TMS | Trimethylsilyl |
| TMSOK | Potassium trimethylsilanolate |

Reaction Schemes below illustrate the methods employed in the synthesis of the compounds of the present invention of formula I. All substituents are as defined above unless indicated otherwise. The synthesis of the novel compounds of formula T which are the subject of this invention may be accomplished by one or more of several similar routes.

In Scheme I, commercially available I-1 is treated with a 1 to 2 M solution of vinyl Grignard in either anhydrous THF or ether at a temperature of 0° C. and allowed to warm to room temperature over a period of time between 1 and 4 hours. The reaction is usually performed in an inert organic solvent such as THF and under an inert atmosphere such as nitrogen. The product is an allylic alcohol of structural formula I-2. Conversion of I-2 to I-3 can be achieved by selecting the desired silyl protecting agent, such as tert-butyl dimethyl chloride, and a weak organic base, such as imidazole, and mixing at room temperature between 4 to 16 hours. Oxidation of the double bond via the bubbling of ozone gas over a period of time until a blue color persists and then reduction of the ozonide by addition of excess methyl sulfide affords the aldehyde I-4. I-4 is then treated with either R-(+)- or S-(−)-2-methyl-2-propanesulfinamide in the presence of a Lewis acid, such as copper sulfate or titanium tetrachloride, which also acts as a drying agent. The reaction is usually performed in an inert organic solvent, such as dichloromethane, between room temperature and 40° C., for a period of 6-36 hours, and the product is the sulfinamide of structural formula I-5. As with I-1, I-5 is treated with vinyl Grignard under similar conditions and time to afford the allyl sulfinamide I-6. To selectively remove the sulfinamide, I-6 is treated with an anhydrous solution of 4 M HCl in dioxane for no more than 15 minutes. The reaction is then diluted with toluene and concentrated to dryness to afford I-7. Finally, I-7 is converted to I-8 via treatment with benzyl chloroformate in the presence of an anhydrous organic base, such as triethyl amine or diisopropyl ethyl amine, in an inert organic solvent, such as DCM, at 0° C., allowing to warm to room temperature over a period of time between 1 to 3 hours.

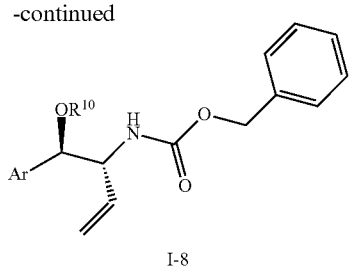

$R^{10}$ = TMS, TBS, TBDPS

Alternatively, aldehyde I-4 can be prepared as shown in Scheme II. Treatment of I-3 with osmium tetraoxide in the presence of N-methyl morpholine N-oxide affords the diol I-9. The reaction is usually performed in a mixture or water and acetone and carefully worked up to remove the toxic osmium tetraoxide before concentrating the solution. The residue, I-9, is then taken up in acetone/water (8:1) and treated with sodium periodate for a period of time between 8 and 24 hours at room temperature to afford the aldehyde I-4 as in Scheme 1. This is then taken to the final desired intermediate I-8 using the same procedures described in Scheme 1.

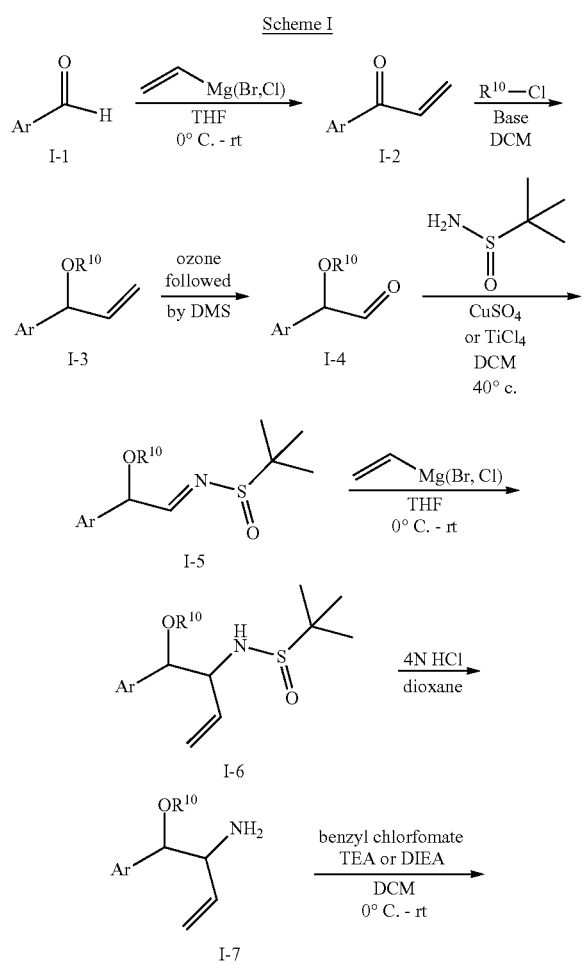

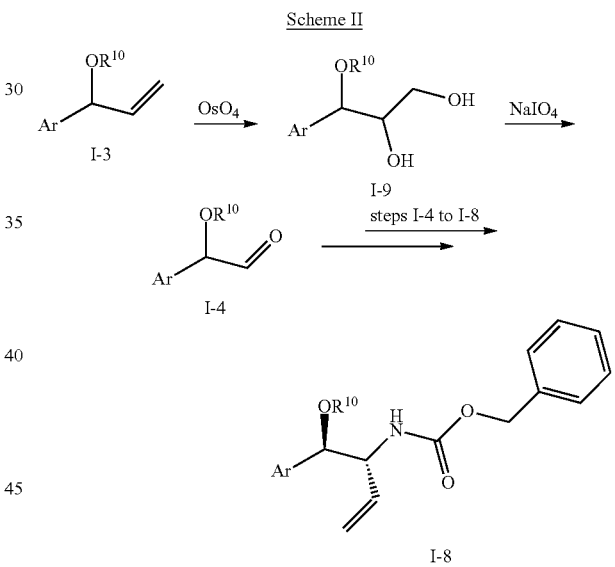

Scheme III describes the synthesis of the pyrrolidine core using the CBz-protected allyl amide I-8 described in Schemes I and II. The vinyl compound I-8 may be reacted in an olefin cross metathesis with the vinyl ketone intermediate I-10 using appropriate catalysts useful in olefin metathesis known to those skilled in the art. Suitable catalysts include, but are not limited to, both "Grubbs" and "Zhan" catalysts and of the type known as Grubbs-II and Zhan I or II to produce the compound of structural formula I-11. Hydrogenation of this intermediate I-11 by treatment with 10% palladium on carbon catalyst under hydrogen atmosphere in a solvent such as ethyl acetate or ethanol over 2-16 hours achieves hydrogenation of the olefin along with removal of any Cbz-protecting groups in addition to a ring closure via an intramolecular inline formation between the free amine and ketone and reduction of the imine to form the pyrrolidine ring of the general structure I-12. Depending on the choice of solvent, halogen substituents on the aryl can either remain or be removed at this time depending on preference of the final intermediate. Selective Hoc protection of the pyrrolidine may be accomplished by the addition of one equivalent of tert-butyl dicarbonate (Boc$_2$O) to I-12 in the presence of an anhydrous organic base, such as triethylamine (TEA). The reaction is usually performed in an inert organic solvent, such as THF, and under an inert atmosphere, such as nitrogen, affording the product of structural formula I-13. Depending upon the choice of an amide, sulfonamide, or urea, I-13 can be converted to each by using the appropriate method known to those skilled in the arts to form those desired compounds. For sulfonamides, I-13 can be treated with the desired sulfonyl chloride containing R$^6$ in the presence of a suitable base, such as pyridine.

As used herein, R$^6$ is selected from (1) hydrogen, (2) C$_1$-C$_{10}$ alkyl optionally substituted with 1 to 5 groups independently selected from halogen, —OR$^a$, —CO$_2$R$^a$ and CONR$^a$R$^b$, (3) phenyl optionally substituted with 1 to 3 groups independently selected from halogen, C$_1$-C$_5$ alkyl optionally substituted with 1 to 5 halogen atoms, and —OR$^a$, and (4) a 5- or 6-membered heterocyclic ring with from 1 to 4 heteroatoms selected from oxygen, sulfur and nitrogen, and wherein said heterocyclic ring is optionally ortho-fused to a benzene ring, and optionally substituted with 1 to 3 groups independently selected from halogen, C$_1$-C$_5$ alkyl optionally substituted with 1 to 5 halogen atoms, and —OR$^a$.

As used herein, het is selected from pyridine, pyrimidine, pyrazine, thiazole, thiophene.

The reaction is usually performed in an inert organic solvent such as DMF, between room temperature and 80° C., for a period of 12-24 h, and the product is the sulfonamide of structural formula I-14. For amides, I-13 can be treated with the desired acetyl chloride containing R$^6$ in the presence of a suitable organic base, such as TEA or DIEA. The reaction is usually performed in an inert organic solvent such as DMF, at room temperature for a period of 12-24 h, and the product is the amide of structural formula I-15. Finally, the urea can be formed by treating I-13 with CDI or phosgene in the presence of an amine containing R$^6$ over a period of time between 1 and 24 h, at room temperature to afford the urea of structural formula I-16. Removal of the Boo and silyl protecting groups of I-14, I-15, and I-16 simultaneously via treatment with 6 M HCl in aqueous methanol at room temperature for a period of 12-24 hours affords the final desired products of the various amide, sulfonamide and urea containing R$^6$ shown in the general structural formulas I-17, I-18 and I-19.

Additional deprotection steps may be included if there are useful protecting groups on the R$^6$ moiety known to those skilled in the art necessary to allow the chemistry to proceed in a facile fashion. These protecting groups may include trityl groups, tert-butylcarbamate groups or other groups suitable for the protection of heterocyclic compounds or the functional groups attached to the R$^6$ group, such as amines, hydroxyls, carboxylic acids, known to those skilled in the art.

Scheme III

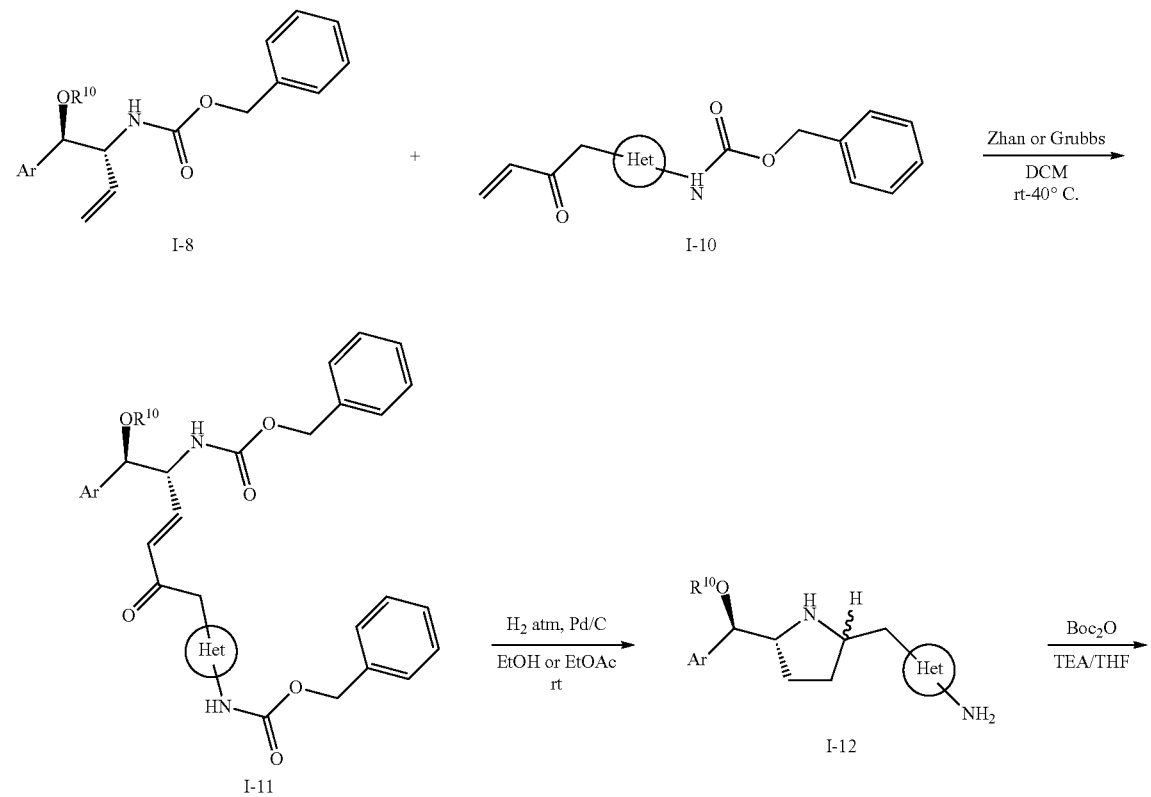

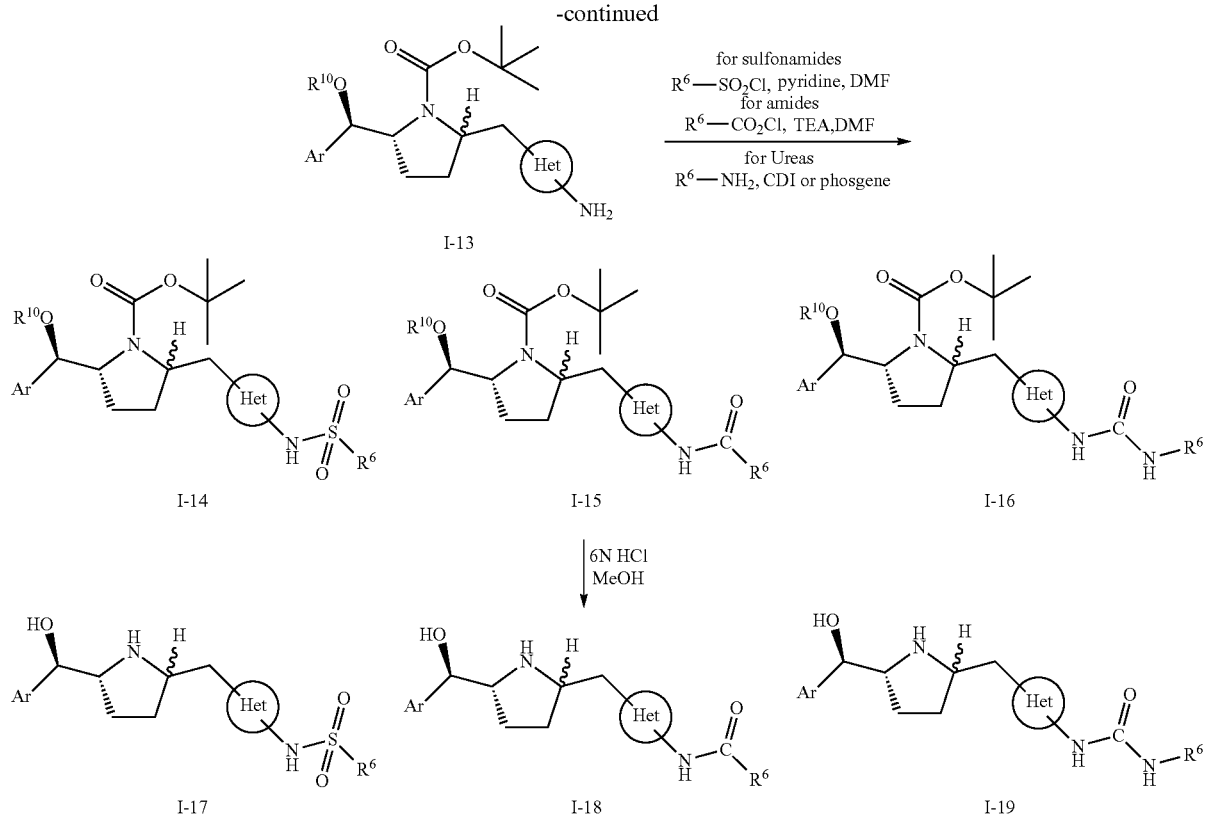

Scheme IV outlines an alternate synthesis of the pyrrolidine core that interconnects schemes I and III routes to provide pyrrolidine core with diastereoselectivity for the cis 2S, 5R pyrrolidine.

The starting 2-amino-arylpropane-1,3-diol (I-20) is first protected as the hemi-acetal using acetone in a suitable solvent such as toluene in the presence of acid such as p-toluene sulfonic acid and then the amine is protected by treatment with tert-butyl dicarbonate to give intermediate I-21. Using standard Swern oxidative conditions, the free primary hydroxyl is converted to the aldehyde I-22. The Wittig reaction is utilized to convert the aldehyde I-22 to the vinyl analog I-23, via treatment with methyl triphenyl phosphonium bromide. After protecting group manipulation, as seen via intermediate I-24, the scheme becomes convergent to scheme III through intermediate I-8. Using similar procedures as described in Scheme III, intermediate I-11 can then be obtained. Optimization of the hydrogenation by introducing hydrochloric acid and a dilution factor of 0.15 to 0.30 M concentration afforded primarily the cis 2S,5R pyrrolidine core I-13a.

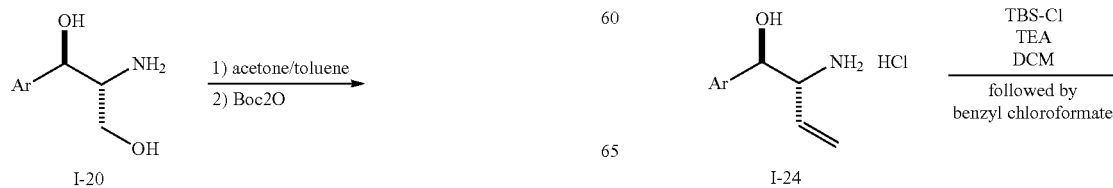

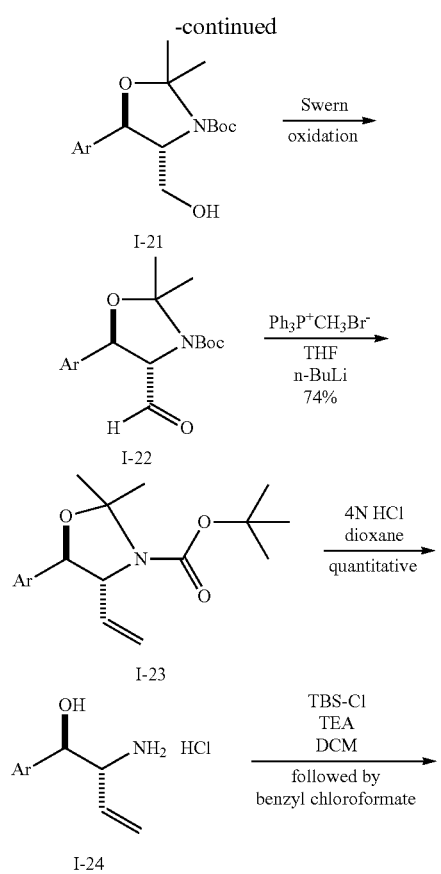

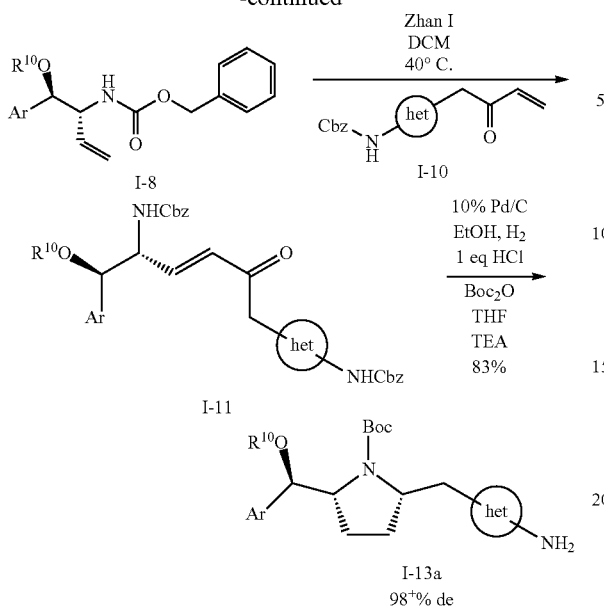

carbamate I-30. The reaction is usually performed in an inert organic solvent, like toluene, under an inert atmosphere, such as nitrogen. This material forms the basis in which the pyrrolidine core can been synthesized.

Scheme V

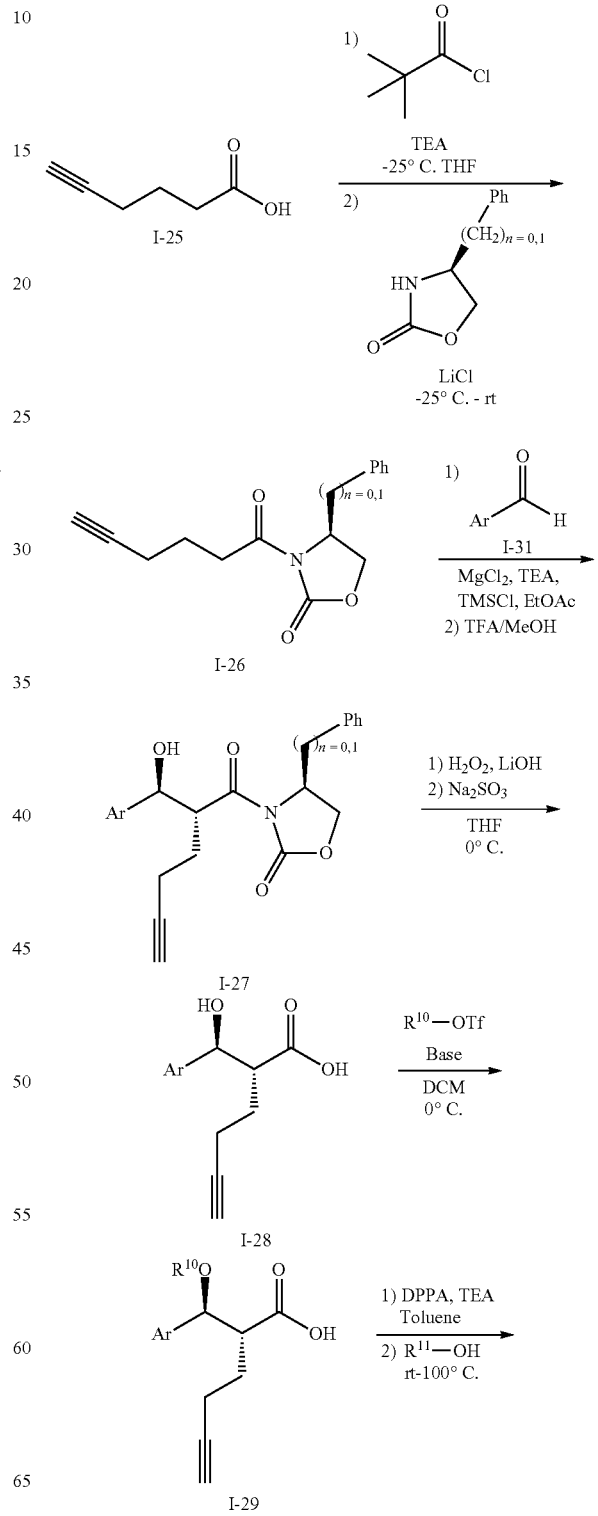

Scheme V outlines the process of synthesizing the acetylene intermediate via aldol chemistry to set the chirality of both the hydroxyl group and left hand portion of the pyrrolidine. From there, this acetylene intermediate can be used to synthesize both the cis and trans pyrrolidines.

Commercially available I-25 is first treated with trimethylacetyl chloride in the presence of a weak organic base such as triethylamine at −25° C. for 2 hours. The sequential addition of anhydrous lithium chloride and either (S)-(−)-4-benzyl or (S)-(−)-4-phenyl-2-oxazolidinone to the mixture followed by gradual warming to room temperature over a period of time between 12 and 24 hours affords imide I-26. The reaction is usually performed in an inert organic solvent, such as THF, under an inert atmosphere, such as nitrogen. The alcohol I-32 is prepared according to published procedures (See Evans et al., *J. Am. Chem. Soc.* 2002, 124, 392-394). For example, treatment of I-26 with anhydrous magnesium chloride, triethylamine, the appropriate aldehyde I-27, such as 3-chlorobenzaldehyde or benzaldehyde, and chlorotrimethylsilane at room temperature over a period of 72 hours yields the trimethylsilyl ether of the aldol product I-27. The reaction is usually performed in an organic solvent such as ethyl acetate under an inert atmosphere such as nitrogen. Treatment of the trimethylsilyl ether intermediate with a trifluoroacetic acid and methanol mixture affords the desired alcohol I-27. The hydrolysis of the imide I-27 is achieved by treatment with lithium peroxide at 0° C. for a period of 15-18 hours. The peroxy acid is subsequently reduced with an aqueous solution of sodium sulfite to afford the carboxylic acid I-28. The reaction is usually performed in a mixture of an inert organic solvent, such as THF, and water under an inert atmosphere, such as nitrogen. Conversion of I-28 to I-29 can be achieved by selecting the desired silyl protecting agent, such as tert-butyl dimethylsilyl trifluoromethanesulfonate, and reacting it in the presence of a weak organic base, such as DBU, at 0° C. for a period of between 12 to 16 hours. I-29 can then be treated with diphenylphosphoryl azide in the presence of a weak organic base such as triethylamine for a period of 6 hours at room temperature. Addition of the appropriate alcohol, such as 4-methoxybenzyl alcohol, with heating to 100° C. for a period between 12 and 16 hours yields the corresponding

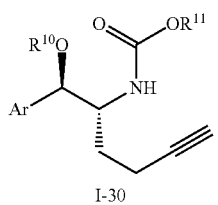

I-30

Scheme VI outlines the use of I-30 for conversion of the pyrrolidine acid core. The pyrrolidine is formed by a ring closer via an intramolecular Michael addition with the alkyne followed by reduction of the imide to form the cis pyrrolidine in high diasteromeric selectivity. Removal of the hydroxyl protection followed by saponification of the ester affords the final desired pyrrolidine acid used for analog synthesis.

The alkyne I-30 may be reacted in a Sonagashira type crosscoupling reaction with the corresponding commercially available heteroaryl halide I-31 to afford I-32 using the appropriate reaction conditions known to those skilled in the art. The reaction conditions can include the use of catalysts, such as tetrakis(triphenylphosphine)-palladium(0), with or without copper(I) iodide in the presence of an organic base, such as triethylamine, or palladium(II) acetate with an organic base, such as tetrabutylammonium acetate, in an organic solvent, such as acetonitrile or DMF, under an inert atmosphere, such as nitrogen. Removal of the amino protection, Moz, in the presence of an acid such as TFA in anhydrous solvent, such as DCM, afforded I-32 without the removal of the silyl protection of the hydroxyl group. Ring closure to the pyrrolidine is accomplished in a two reaction sequence. First I-32 undergoes an intramolecular Michael addition of the amine to the alkyne in the presence of a catalyst such as palladium acetate or platinum chloride refluxed in toluene. Then after removal of the solvent, the resulting imide is reduce to the amine (pyrrolidine) I-33 in the presence of a palladium catalyst such as 10% palladium on carbon under hydrogen atmosphere in either methanol or ethanol. Treatment of the free amine with tert-butyl carbonate in the presences of an organic base such as TEA or DIEA affords the Boc protected intermediate I-34. Then removal of the silyl group with TBAF followed by saponification of the ester to the acid in presence of a strong base gives the desired pyrrolidine acid core I-35 for multiple analog synthesis.

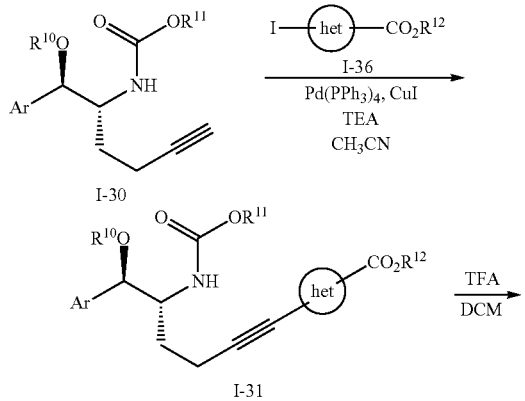

Scheme VI

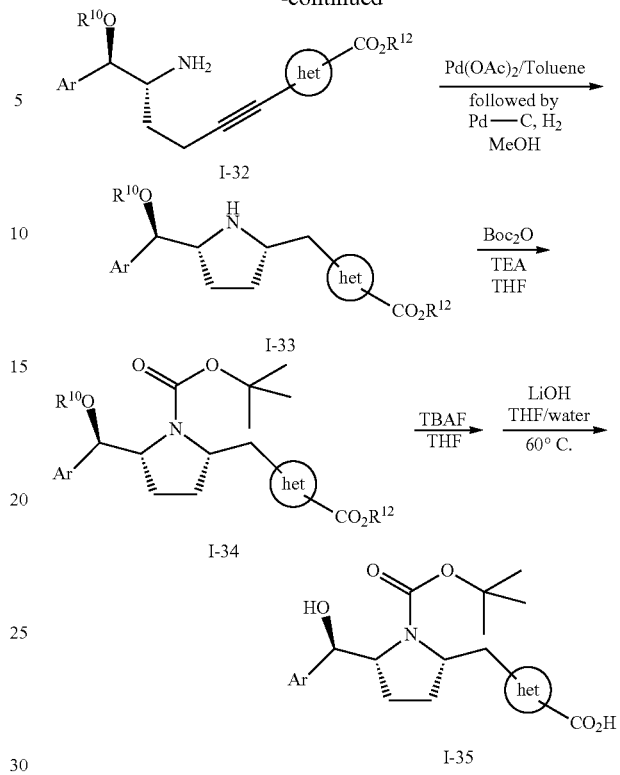

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Biological Assays: The following in vitro assays are suitable for screening compounds that have selective β3 agonist activity:

Functional Assay: cAMP production in response to ligand is measured according to Barton, et al. (1991, Agonist-induced desensitization of D2 dopamine receptors in human Y-79 retinoblastoma cells. Mol. Pharmacol. v3229:650-658) modified as follows. cAMP production is measured using a homogenous time-resolved fluorescence resonance energy transfer immunoassay (LANCE™, Perkin Elmer) according to the manufacture's instructions. Chinese hamster ovary (CHO) cells, stably transfected with the cloned β-adrenergic receptor (β1, β2 or β3) are harvested after 3 days of subculturing. Harvesting of cells is done with Enzyme-free Dissociation Media (Specialty Media). Cells are then counted and resuspended in assay buffer (Hank's Balanced salt solution supplemented with 5 mM HEPES, 01% BSA) containing a phosphodiesterase inhibitor (IBMX, 0.6 mM). The reaction is initiated by mixing 6,000 cells in 6 μL with 6 μL Alexa Fluor labeled cAMP antibody (LANCE™ kit) which is then added to an assay well containing 12 μL of compound (diluted in assay buffer to 2× final concentration). The reaction proceeds for 30 minutes at room temperature and is terminated by the addition of 24 ul detection buffer (LANCE™ kit). The assay plate is then incubated for 1 hour at room temperature and time-resolved fluorescence measured on a Perkin Elmer Envision reader or equivalent. The unknown cAMP level is determined by comparing fluorescence levels to a cAMP standard curve.

The non-selective, full agonist β3-adrenergic ligand isoproterenol is used at all three receptors to determine maximal stimulation. The human β3 adrenergic receptor (AR) selective ligand (S)—N-[4-[2-[[2-hydroxy-3-(4-hydroxyphenoxy)propyl]amino]ethyl]-phenyl]-4-iodobenzenesulfonamide is used as a control in all assays. Isoproterenol is titrated at a final concentration in the assay of $10^{-10}$ M to $10^{-5}$ M and the selective ligand (S)—N-[4-[2-[[2-hydroxy-3-(4-hydroxyphenoxy)propyl]amino]ethyl]phenyl]-4-iodobenzenesulfonamide is titrated at the β3 receptor at concentration of $10^{-10}$ M to $10^{-5}$ M. Unknown ligands are titrated at all 3 β-adrenergic receptor subtypes at a final concentration in the assay of $10^{-10}$ M to $10^{-5}$ M to determine the $EC_{50}$. The $EC_{50}$ is defined as the concentration of compound that gives 50% activation of its own maximum.

Binding Assay: Compounds are also assayed at the β1 and β2 receptors to determine selectivity. All binding assays are run using membranes prepared from CHO cells recombinantly expressing β1 or β2 receptors. Cells are grown for 3-4 days post splitting; the attached cells are washed with PBS and then lysed in 1 mM Tris, pH 7.2 for 10 minutes on ice. The flasks are scraped to remove the cells and the cells then homogenized using a Teflonglass homogenizer. Membranes are collected by centrifuging at 38,000×g for 15 minutes at 4° C. The pelleted membranes are resuspended in TME buffer (50 mM Tris, pH 7.4, 5 mM $MgCl_2$, 2 mM EDTA) at a concentration of 1 mg protein/mL. Large batches of membranes can be prepared, aliquoted and stored at −70° C. for up to a year without loss of potency. The binding assay is performed by incubating together membranes (2-5 µg of protein), the radiolabelled tracer $^{125}$I-cyanopindolol ($^{125}$I-CYP, 45 pM), 200 ug of WGA-PVT SPA beads (GE Healthcare) and the test compounds at final concentrations ranging from 10-10 M to 10-5 M in a final volume of 200 µL of TME buffer containing 0.1% BSA. The assay plate is incubated for 1 hour with shaking at room temperature and then placed in a Perkin Elmer Trilux scintillation counter. The plates are allowed to rest in the Trilux counter for approximately 10 hours in the dark prior to counting. Data are analyzed using a standard 4-parameter non-linear regression analysis using either Graphpad Prism software or an internally developed data analysis package. The $IC_{50}$ is defined as the concentration of the compound capable of inhibiting 50% of the binding of the radiolabelled tracer ($^{125}$I-CYP). A compound's selectivity for the β3 receptor may be determined by calculating the ratio ($IC_{50}$ β1 AR, β2 AR)/($EC_{50}$ β3 AR).

In some cases the order of carrying out the foregoing reaction schemes may be varied to facilitate the reaction or to avoid unwanted reaction products. The following examples are provided so that the invention can be more fully understood. These examples are illustrative only and should not be construed as limiting the invention in any way.

Intermediate 1

Benzyl[6-(2-oxobut-3-en-1-yl)pyridin-2-yl]carbamate (i-1)

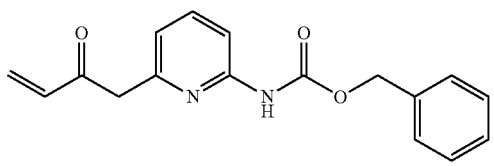

i-1

Step A: N-methoxy-N-methyl-2-(6-nitropyridin-2-yl)acetamide

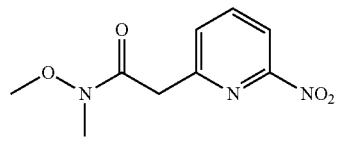 [SMILES: CON(C)C(=O)Cc1cccc([N+](=O)[O-])n1]

To a suspension of 250 mg (1.37 mmol) of (6-nitropyridin-2-yl) acetic acid in 6 mL of dichloromethane was added DIEA (0.72 mL, 4.12 mmol) which resulted in some exotherming (+5° C.) and the suspension becoming a solution. After 2 min cooling, HOBt (263 mg, 1.72 mmol), N,O-dimethylhydroxylamine HCl (167 mg, 1.72 mmol) was added to the solution followed by EDC (329 mg, 1.72 mmol) and the resulting mixture stirred at room temperature overnight under nitrogen atmosphere. The solution was transferred to a separatory funnel and washed with 1 M HCl which caused an emulsion. Methanol was added to break up the emulsion and the aqueous was partitioned off. The organics were dried over sodium sulfate, filtered and concentrated under vacuum. Purification via preparative TLC plate (2×1000 µM) eluting with 50% ethyl acetatehexane afforded the title compound (236 mg, 76%) as a white solid. LC-MS: $C_9H_{11}N_3O_4$ calculated 225.20 found m/z (ES) 226 (MH)$^+$. $^1$HNMR (500 MHz, DMSO) δ:8.56 (d, J=2.0 Hz, 1H), 8.25 (d, J=8.4 Hz, 1H), 8.04 (dd, J=2.0, 8.3 Hz, 1H), 4.02 (br s, 2H), 3.88 (s, 3H), 3.07 (s, 3H).

Step B: 2-(6-aminopyridin-2-yl) N-methoxy-N-methylacetamide

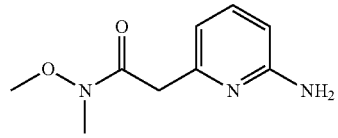

To a solution of N-methoxy-N-methyl-2-(6-nitropyridin-2-yl)acetamide (200 mg, 0.88 mmol) in 4 ml ethanol was added palladium on carbon (25 mg) and the resulting mixture set under hydrogen atmosphere and stirred vigorously at room temperature for 2 hours. The catalyst was filtered off using a 0.45 mM Oilmen PTFE syringe filter washing the solid with 10 mL of methanol. The filtrate was concentrated to dryness under reduced pressure and used for the next reaction without further purification (84.4 mg, 53%). LC-MS: $C_9H_{13}N_3O_2$ calculated 195.22 found m/z (ES) 196 (MH)$^+$.

Step C: benzyl (2E)-2-([[(benzyloxy)carbonyl]imino)-6-(2-[methoxy(methyl)amino]-2-oxoethyl)pyridine-1(2H)-carboxylate

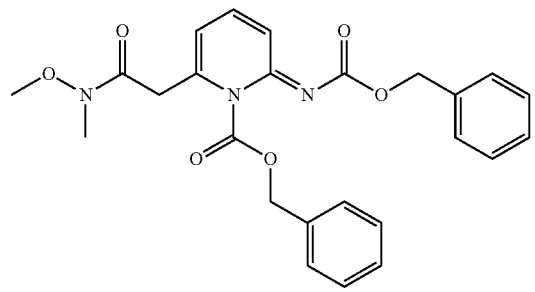 [SMILES: CON(C)C(=O)Cc1ccc/c(=N\C(=O)OCc2ccccc2)n1C(=O)OCc1ccccc1]

To a solution of 2-(6-aminopyridin-2-yl) N-methoxy-N-methylacetamide (84.4 mg, 0.43 mmol) in DCM (15 ml) was added DIEA (0.114 ml, 0.65 mmol) and the resulting mixture cooled via ice/water bath to 0° C. Benzyl chloroformate (0.08 ml, 0.60 mmol) was added after 5 minutes and the resulting solution stirred for 1 hour allowing to warm to room temperature. The major product was observed to be the di-Cbz protected intermediate via LC-MS and TLC. Therefore, an additional 1 eq of benzyl chloroformate was added to ensure that all the product was converted to the di-CBz product. The reaction was quenched with water (10 ml) and extracted with DCM (2×10 mL). The organics were combined, washed with water (5 mL) and brine (5 mL), dried over sodium sulfated, filtered, and concentrated under reduced pressure. The residue was purified by preparative TLC plate (1000 μM) eluting with 25% ethyl acetate in hexane to afforded the title compound (170.4 mg, 85%). LC-MS: $C_{25}H_{25}N_3O_6$ calculated 463.48 found m/z (ES) 464 (MH)$^+$ and 330 (M-Cbz)$^+$.

Step D: Benzyl[6-(2-oxobut-3-en-1-yl)pyridin-2-yl]carbamate (i-1)

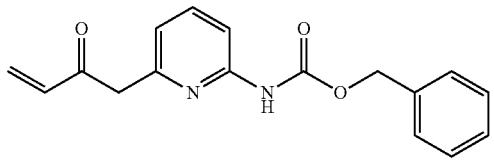 [SMILES: C=CC(=O)Cc1cccc(NC(=O)OCc2ccccc2)n1]

To a solution of benzyl (2E)-2-([(benzyloxy)carbonyl]imino)-6-(2-[methoxy(methyl)amino]-2-oxoethyl)pyridine-1(2H)-carboxylate (150 mg, 0.33 mmol) in 4 ml anhydrous THF cooled to −40° C. via dry ice/acetone bath under nitrogen atmosphere was added via syringe 1.0M vinylmagnesium bromide (1.5 mL, 1.5 mmol) and the resulting solution stirred for 2 hours allowing to warm to room temperature. The reaction was quenched with water and extracted with ethyl acetate (3×10 mL). The organics were combined, dried over sodium sulfate, filtered, and concentrated under reduced pressure. The residue was purified via preparative TLC plate (1000 μM) eluting with 2.5% methanol in dichloromethane to afford the title compound (64 mg, 67%). LC-MS: $C_{17}H_{16}N_2O_3$ calculated 296.32 found m/z (ES) 297.3 (MH)$^+$. $^1$HNMR (500 MHz, DMSO) δ: 10.12 (s, 1H) 8.05 (d, J=8.5 Hz, 1H), 7.99 (d, J=2.1, 1H), 7.62 (dd, J=2.2, 8.7 Hz, 1H), 7.60-7.34 (m, 5H), 6.40 (dd, J=10.3, 17.7 Hz, 1H), 6.26 (dd, J=10.3, 18.1 Hz, 1H), 5.94 (d, J=10.3 Hz, 1H), 5.22 (s, 2H), 3.60 (s, 2H).

Intermediate 2

(1R)-1-[(R)-{[tert-butyl(dimethyl)silyl]oxy}phenyl)methyl]prop-2-en-1-yl}carbamate (i-2

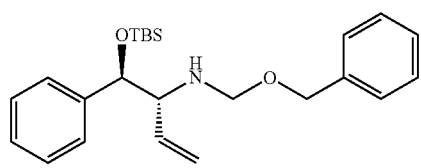

Step A: tert-butyl (4R,5R)-4-(hydroxymethyl)-2-2-dimethyl-5-phenyl-1,3-oxazolidine-3-carboxylate

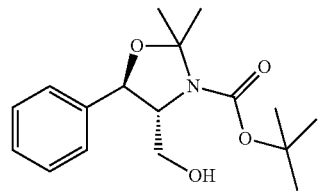 [SMILES: CC(C)(C)OC(=O)N1[C@H](CO)[C@@H](c2ccccc2)OC1(C)C]

A solution of commercially available (1R,2R)-2-amino-1-phenylpropane-1,3-diol (86.2 g, 516 mmol) in toluene (400 mL) and acetone (100 mL) was refluxed with a Dean-Stork trap for 5 hours. After removal of the solvent under vacuum, the residue was dissolved in 300 mL of anhydrous THF and a solution of tert-butyl dicarbonate (123.8 g, 567 mmol) in THF (100 mL) was added. The resulting mixture was stirred at room temperature for 5 hours. The solvent was removed under reduced pressure and the residue purified via Biotage Flash 75 (silica gel cartridge) eluting with a gradient of 0-30% ethyl acetate in hexane to afford the title compound (155.4 g, 98%) as a clear oil which upon time in the refrigerator crystallized. LC-MS: $C_{17}H_{25}NO_4$ calculated 307.18 found m/z (ES) 308.1 (MH)$^+$, 208.2 (M-Boc)$^+$, and 330.2 (MNa)$^+$.

Step B: tert-butyl (4S,5R)-4-formyl-2-2-dimethyl-5-phenyl-1,3-oxazolidine-3-carboxylate

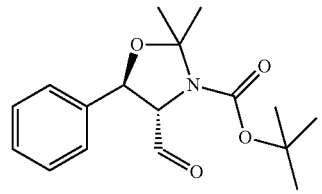 [SMILES: CC(C)(C)OC(=O)N1[C@H](C=O)[C@@H](c2ccccc2)OC1(C)C]

A solution of DMSO (105.1 mL, 1480 mmol) in dichloromethane (250 mL) was added a solution of oxalyl chloride (54.6 mL, 626 mmol) at −78° C. in DCM (500 mL) over a period of one hour and the resulting mixture was stirred for one hour at −78° C. To this mixture was then added a solution of tert-butyl (4R,5R)-4-(hydroxymethyl)-2-2-dimethyl-5-phenyl-1,3-oxazolidine-3-carboxylate (155.4 g, 510 mmol) in dichloromethane (400 mL) via addition funnel over a period of 45 minutes and the resulting solution stirred for 30 minutes. The mixture was warmed to −15° C. and TEA (397 mL, 2850 mmol) was added slowly over a period of 45 minutes. The solution became very thick and did not stir well. The reaction mixture was then allowed to warm to 0° C. over a period of 5 hour and then it was poured into 1000 mL of 1.0M aqueous ammonium chloride. The organic layer was separated and the aqueous extracted with dichloromethane (2×500 mL). The combined organics were then washed with water (2×500 mL), dried over sodium sulfate, filtered, and concentrated under vacuum to afford the crude aldehyde (164 g, 100%), used without further purification for the next step. $^1$HNMR (500 MHz, CDCl$_3$) δ: 9.52 (br d, J=10 Hz, 1H) 7.33-7.20 (m, 5H), 5.04 (br s, 1H), 3.51-3.45 (m, 1H), 1.67 (s, 3H), 1.55 (s, 3H), 1.43 (s, 9H).

Step C: tert-butyl (4R,5R)-2-2-dimethyl-5-phenyl-4-vinyl-1,3-oxazolidine-3-carboxylate

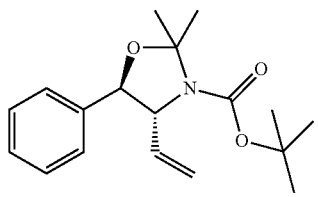 [SMILES: C=C[C@@H]1[C@@H](c2ccccc2)OC(C)(C)N1C(=O)OC(C)(C)C]

To a solution of methyltriphenylphosphonium bromide (164 g, 458 mmol) in THF (500 mL) at 0° C. was added BuLi (183 mL, 458 mmol), and the resulting mixture was stirred at 0° C. for 30 minutes. Then a solution of tert-butyl (4S,5R)-4-formyl-2-2-dimethyl-5-phenyl-1,3-oxazolidine-3-carboxylate (70 g, 229 mmol) in 100 mL anhydrous THF was added, and the reaction mixture was stirred at 0° C. for 2 hours, then allowed to warm to room temperature while it stirred overnight. Solid precipitate was filtered off and the filtrate was washed with water (2×100 mL). The organics were then dried over magnesium sulfate, filtered, and concentrated under reduced pressure. The residue was purified via Biotage Flash 75 (silica gel cartridge) eluting with a gradient of 0-30% ethyl acetate in hexane to afford the title compound (46.6 g, 72%). LC-MS: $C_{18}H_{25}NO_3$ calculated 303.20 found m/z (ES) 304.3 (MH)$^+$.

Step D: (1R,2R)-2-amino-1-phenylbut-3-en-1-ol

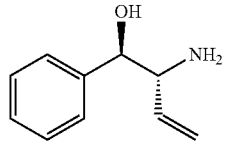

A pre-mixed solution of 10% aqueous 4N HCl in dioxane (33 mL $H_2O$ in 330 mL 4N HCl in dioxane) was cooled to 0° C. using an ice/water bath. This solution was then cannulated over to a 1000 mL round bottom flask containing tert-butyl (4R,5R)-2-2-dimethyl-5-phenyl-4-vinyl-1,3-oxazolidine-3-carboxylate (40 g, 132 mmol) and the resulting mixture stirred for 2 hours allowing to warm to room temperature. The mixture was then diluted with toluene (300 mL) and concentrated to dryness under reduced pressure. The residue was then azeotroped with toluene (2×250 mL) to remove all trace of water. This afforded the title compound (26.2 g 100%) which was used for the following step without the need for further purification. LC-MS: $C_{10}H_{13}NO$ calculated 163.12 found m/z (ES) 164.1 (MH)$^+$.

Step E: (1R,2R)-1-([tert-butyl(dimethyl)silyl]oxy)-1-phenylbut-3-en-2-amine

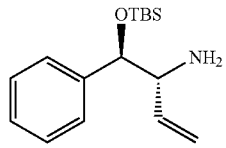

To a solution of (1R,2R)-2-amino-1-phenylbut-3-en-1-ol (23 g, 115 mmol) in dichloromethane (300 mL) cooled to 0° C. via ice/water bath was added TEA (32.1 mL, 230 mmol) and the resulting mixture set under nitrogen atmosphere with addition funnel attached. The addition funnel was charged with a solution of tert-butyl-chloride (17.4 g, 115 mmol) in 100 mL dichloromethane which was then added dropwise to the mixture to maintain the temperature at 0° C. Once all was added, the resulting solution was stirred for 30 minutes at 0° C. and then allowed to warm to room temperature and stirred an additional 2 hours. The solution was washed with aqueous 0.1M HCl (200 mL) and then washed with brine (200 mL). The organic layer was then dried over sodium sulfate, filtered, and the filtrate concentrated under vacuum. The residue was the purified via Biotage Flash 75 (silica gel cartridge) eluting with a gradient of 0-10% methanol in dichloromethane to afford the title compound (29.0 g, 91%). LC-MS: $C_{16}H_{27}NOSi$ calculated 277.26 found m/z (ES) 278.2 (MH)$^+$.

Step F: ((1R)-1-[(R)-{[tert-butyl(dimethyl)silyl]oxy} phenyl)methyl]prop-2-en-1-yl}carbamate (i-2)

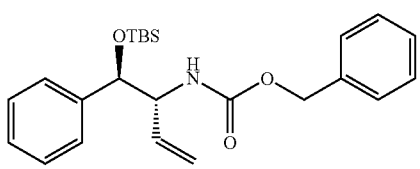

i-2

To a cooled solution (0° C.) of (1R,2R)-1-([tert-butyl(dimethyl)silyl]oxy)-1-phenylbut-3-en-2-amine (28.0 g, 101 mmol) in dichloromethane (600 mL) was added DIEA (22 mL, 126 mmol) and the resulting mixture set under nitrogen atmosphere with addition funnel attached. The addition funnel was charged with a solution of benzylchloroformate (15.9 mL, 111 mmol) in 100 mL dichloromethane which was then added dropwise to the mixture to maintain the temperature of less than 5° C. After complete addition, the solution was stirred at <5° C. for 30 minutes and then allowed to warm to room temperature and stirred for an additional 2 hours. The solution was washed with water (100 mL) and then the aqueous extracted with dichloromethane (100 mL). The organics were then combined, dried over sodium sulfate, filtered, and the filtrate concentrated under vacuum. The residue was the purified via Biotage Flash 75 (silica gel cartridge) eluting with a gradient of 0-40% ethyl acetate in hexane to afford the title compound (36.1 g, 87%). LC-MS: $C_{24}H_{33}NO_3Si$ calculated 411.31 found m/z (ES) 412.2 (MH)$^+$. $^1$HNMR (500 MHz, CDCl$_3$) δ: 7.33-7.25 (m, 3H), 7.21-7.18 (m, 2H), 5.89 (ddd, J=7.1, 10.3, 17.4 Hz, 1H), 5.20 (d, J=10.4 Hz, 1H), 5.18 (d, J=17.4 Hz, 1H), 4.72 (d, J=4.2 Hz, 1H), 3.88-3.82 (m, 1H), 3.29 (d, J=9.4 Hz, 1H), 1.20 (s, 9H), 0.94 (s, 9H), 0.09 (s, 3H), −0.13 (s, 3H).

Intermediate 3

Tert-butyl(2S,5R)-2-[(6-aminopyridin-3-yl)methyl]-5-[(R)-hydroxy(phenyl)methyl]pyrrolidine-1 carboxylate

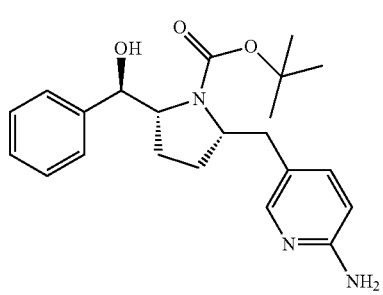

i-3

Step A: Benzyl[5-{(3E,5R,6R)-5-{[(benzyloxy)carbonyl]amino}-6-{[tert-butyl(dimethyl)silyl]oxy}-2-oxo-6-phenylhex-3-en-1-yl)pyridin-2-yl]carbamate

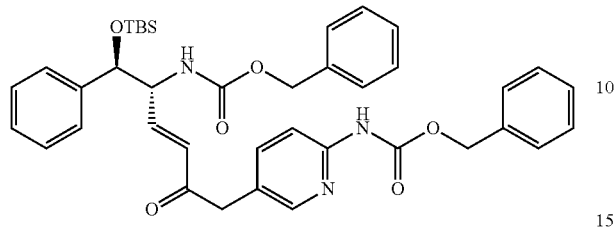

To a solution of benzyl[6-(2-oxobut-3-en-1-yl)pyridin-2-yl]carbamate (i-1, 639 mg, 2.16 mmol) and ((1R)-1-[(R)-{[tert-butyl(dimethyl)silyl]oxy)phenyl)methyl]prop-2-en-1-yl}carbamate (i-2) (600 mg, 1.44 mmol) in 7 mL of anhydrous dichloromethane was added the Zhan I catalyst (240 mg, 0.36 mmol) and the resulting green solution was heated to 40° C. overnight under nitrogen atmosphere. The reaction was concentrated to dryness and the residue purified via preparative plates (4×1000 μM) eluting with 7.5% ethyl acetate in DCM to afford the title compound (225 mg, 23%). LC-MS: $C_{39}H_{45}N_3O_6Si$ calculated 679.31 found m/z (ES) 680.3 $(MH)^+$.

Step B: 5-({(5R)-5-[(R)-([tert-butyl(dimethyl)silyl]oxy}(phenyl)methyl]pyrrolidin-2-yl}methyl)pyridin-2-amine

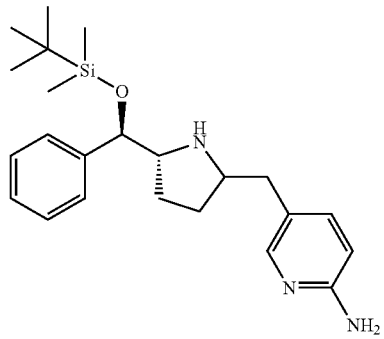

To a solution of 210 mg (0.31 mmol) Benzyl[54(3E,5R,6R)-5-{[(benzyloxy)carbonyl]amino}-6-{[tert-butyl(dimethyl)silyl]oxy}-2-oxo-6-phenylhex-3-en-1-yl)pyridin-2-yl]carbamate (from Step A above) in 3 mL ethanol was added 10% palladium on carbon (30 mg) and 1.25 M HCl in methanol (0.25 mL, 0.31 mmol) and the resulting suspension was set under hydrogen atmosphere via a balloon of hydrogen gas. The reaction was stirred under hydrogen for 20 hours at room temperature. TLC proved that the reaction was complete. The catalyst was filtered off using a Gilmen 0.45 μM PTFE syringe filter and washed with ethanol (4×5 mL). The filtrate was concentrated to dryness under vacuum and the residue purified by preparative plate (2×1000 μM) eluding with 10% methanol in dichloromethane to afford the title compound (121 mg, 99%). LC-MS: $C_{23}H_{35}N_3OSi$ calculated 397.23 found m/z (ES) 398.2 $(MH)^+$.

Step C: Tert-butyl(2S,5R)-2-[(6-aminopyridin-3-yl)methyl]-5-[(R)-{[tert-butyl(dimethyl)silyl]oxy}(phenyl)methyl]pyrrolidine-1-carboxylate

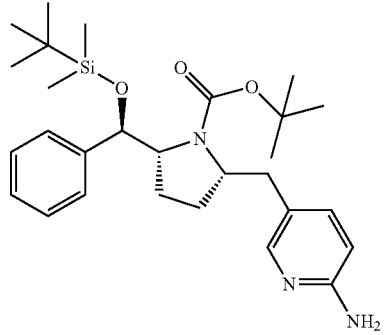 [SMILES: CC(C)(C)OC(=O)N1[C@H](Cc2ccc(N)nc2)CC[C@@H]1[C@H](O[Si](C)(C)C(C)(C)C)c1ccccc1]

To a solution of 121 mg (0.30 mmol) of 5-({(5R)-5-[(R)-([tert-butyl(dimethyl)silyl]oxy}(phenyl)methyl]pyrrolidin-2-yl}methyl)pyridin-2-amine in 5 mL of anhydrous THF (from Step B above) was added tert-butyl carbonate (66 mg, 0.30 mmol), followed by TEA (42 μL, 0.30 mmol) and the resulting solution stirred at room temperature under nitrogen atmosphere overnight. The reaction mixture was put directly on a preparative plate (1500 μM) and eluted with 60% ethyl acetate in hexane to afford the title compound (40.3 mg, 27%). LC-MS: $C_{28}H_{43}N_3O_3Si$ calculated 497.23 found m/z (ES) 498.2 $(MH)^+$ and 398.2 $(M-Boc)^+$.

Step D: Tert-butyl(2S,5R)-2-[6-aminopyridin-3-yl)methyl]-5-[(R)-hydroxy(phenyl)methyl]pyrrolidine-1-carboxylate

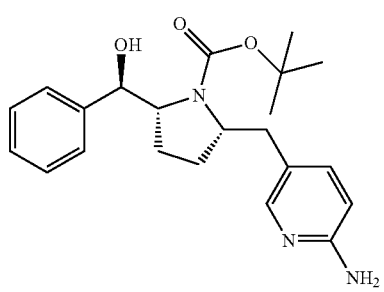

i-3

To a solution tert-butyl(2S,5R)-2-[(6-aminopyridin-3-yl)methyl]-5-[(R)-{[tert-butyl(dimethyl)silyl]oxy}(phenyl)methyl]pyrrolidine-1-carboxylate (40 mg, 0.08 mmol) in THF (0.5 mL) was added 1.0M solution of TBAF in THF (1 mL, 1.0 mmol) and the resulting solution stirred for an hour at room temperature. The mixture was concentrate under vacuum and the residue taken up in dichloromethane (10 mL). The solution was washed with water (5 mL) and brine (5 mL). The organics were then dried over sodium sulfate, filtered, and concentrated under vacuum. The residue was purified vial preparative TLC plate (1000 μM) eluting with 5% methanol in dichloromethane to afford the title compound as a white foam (25.2 mg, 92%). LC-MS: $C_{22}H_{29}N_3O_3$ calculated 338.23 found m/z (ES) 339.2 (MH) and 239.2 $(M-Boc)^+$.

Intermediate 4

5-({(2S,5R)-1-(tert-butoxycarbonyl)-5-[(R)-hydroxy(phenyl)methyl]pyrrolidin-2-yl}methyl)pyridine-2-carboxylic acid

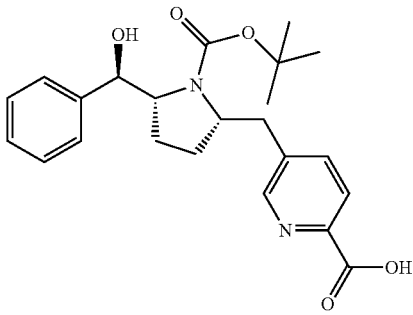

Step A: (4S)-3-Hex-5-ynoyl-4-phenyl-1,3-oxazolidin-2-one

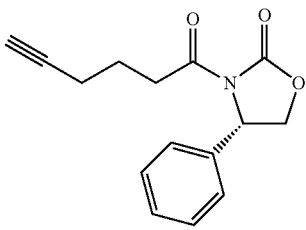 [SMILES: C#CCCCC(=O)N1C(=O)OC[C@@H]1c1ccccc1]

To a solution of 69.0 g (615 mmol) of 5-hexynoic acid and 214 mL (1540 mmol) of triethylamine in 1.0 L of anhydrous tetrahydrofuran at −25° C. under an atmosphere of nitrogen was added 83.0 mL (677 mmol) of trimethylacetyl chloride over 20 min. Upon addition a white precipitate formed and the resulting suspension was stirred for 2 h. Next, 28.7 g (677 mmol) of anhydrous lithium chloride and 100.0 g (615.0 mmol) of (4S)-4-phenyl-1,3-oxazolidin-2-one were added sequentially and the mixture was allowed to gradually warm to ambient temperature over 12 h. All volatiles were removed in vacuo and the residue was diluted with water (1 L) and extracted with ethyl acetate (3×300 mL). The combined organic layers were washed with brine (250 mL), dried over magnesium sulfate, filtered and concentrated in vacuo. The crude residue was purified by silica gel chromatography eluting with a 5-50% ethyl acetate in hexanes gradient to afford the title compound as a colorless solid (135 g, 85.4%). $^1$H NMR (500 MHz, CDCl$_3$): δ 7.40-7.37 (m, 2H), 7.36-7.32 (m, 1H), 7.31-7.28 (m, 2H), 5.42 (dd, J=8.9, 3.7 Hz, 1H), 4.69 (t, J=8.9 Hz, 1H), 4.28 (dd, J=9.2, 3.7 Hz, 1H), 3.13-3.02 (m, 2H), 2.24-2.21 (m, 2H), 1.94 (t, J=2.6 Hz, 1H), 1.84 (quintet, J=7.1 Hz, 2H). LC-MS: m/z (ES) 258.2 (MH)$^+$.

Step B: (4S)-3-{(2R)-2-[(S)-Hydroxy(phenyl)methyl]hex-5-ynoyl}-4-phenyl-1,3-oxazolidin-2-one

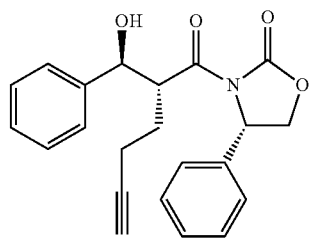 [SMILES: C#CCC[C@@H](C(=O)N1C(=O)OC[C@@H]1c1ccccc1)[C@H](O)c1ccccc1]

To a stirred solution of 56.8 g (221 mmol) of (4S)-3-hex-5-ynoyl-4-phenyl-1,3-oxazolidin-2-one from step A above in 265 mL of anhydrous ethyl acetate at ambient temperature under an atmosphere of nitrogen was added 6.31 g (66.2 mmol) of anhydrous magnesium chloride, 61.5 mL (442 mmol) of triethylamine, 26.9 mL (265 mmol) of benzaldehyde and 42.3 mL (331 mmol) of chlorotrimethylsilane and the resulting mixture was stirred for 72 h. The heterogeneous reaction mixture was filtered through a 300 mL plug of silica gel eluting with an additional 1 L of ethyl acetate. The filtrate was evaporated to dryness in vacuo and the residue suspended in 265 mL of methanol and 10 mL of trifluoroacetic acid. The resulting mixture was stirred at ambient temperature under nitrogen for 5 hours during which time the reaction became homogeneous. All volatiles were then removed in vacuo and the residue was purified by silica gel chromatography eluting with a 5-15% ethyl acetate in hexanes gradient to afford the title compound as a white solid (65.0 g, 81.2%). $^1$H NMR (500 MHz, CDCl$_3$): δ 7.30-7.28 (m, 8H), 7.09-7.07 (m, 2H), 5.42 (dd, J=8.7, 3.7 Hz, 1H), 4.76-4.72 (m, 1H), 4.72-4.67 (m, 1H), 4.65 (t, J=8.7 Hz, 1H), 4.18 (dd, J=8.7, 3.7 Hz, 1H), 3.05 (d, J=7.8 Hz, 1H), 2.24 (td, J=7.1, 2.5 Hz, 2H), 2.00-1.93 (m, 2H), 1.67-1.61 (m, 1H). LC-MS: m/z (ES) 346.1 (MH-H$_2$O)$^+$, 386.0 (MNa)$^+$.

Step C: (2R)-2-[(S)-Hydroxy(phenyl)methyl]hex-5-ynoic acid

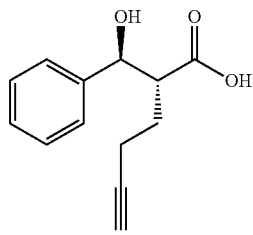 [SMILES: C#CCC[C@@H](C(=O)O)[C@H](O)c1ccccc1]

To a stirred solution of 65.0 g (179 mmol) of (4S)-3-{(2R)-2-[(S)-hydroxy(phenyl)methyl]hex-5-ynoyl}-4-phenyl-1,3-oxazolidin-2-one from Step B above in 1050 mL of a 20 to 1 mixture of anhydrous tetrahydrofuran to water at 0° C. under an atmosphere of nitrogen was added 77.0 mL (894 mmol) of a 35% aqueous hydrogen peroxide solution at a rate slow enough to keep the internal temperature below 3° C. Next, 395 mL (395=top of a 1.0 M aqueous lithium hydroxide solution was added at a rate slow enough to keep the internal temperature of the reaction below 5° C. and the resulting mixture was stirred for 3 h at 0° C. The reaction was quenched with 755 mL (984 mmol) of a 1.3 M aqueous sodium sulfite solution at a rate slow enough to keep the internal temperature of the mixture below 5° C. All volatiles were removed in vacuo and the remaining aqueous phase was extracted with ethyl acetate (3×200 mL). The aqueous phase was then cooled to 0° C. and acidified with a 6 M aqueous hydrogen chloride solution until a pH of 3 was achieved. The aqueous phase was then extracted with ethyl acetate (3×300 mL) and the combined organics were washed with brine (100 ml), dried over magnesium sulfate, filtered and evaporated in vacuo. The residue was purified by silica gel chromatography eluting with a 5-10% ethyl acetate and 3% acetic acid in hexanes gradient to afford the title compound as a colorless gum (32.0 g, 82.0%). $^1$H NMR (500 MHz, CDCl$_3$): δ 7.39-7.28 (m, 5H), 4.85 (d, J=8.2, 1H), 3.03-2.97 (m, 1H), 2.29-2.15 (m, 2H), 1.97 (t, J=2.5 Hz, 1H), 1.93-1.82 (m, 1H), 1.62-1.55 (m, 1H). LC-MS: m/z (ES) 201.0 (MH-H$_2$O)$^+$.

Step D: (2R)-2-[(S)-{[Tert-butyl(dimethyl)silyl]oxy}(phenyl)methyl]hex-5-ynoic acid

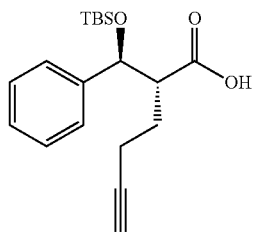 [SMILES: C#CCC[C@@H](C(=O)O)[C@H](O[Si](C)(C)C(C)(C)C)c1ccccc1]

To a stirred solution of 32.0 g (147 mmol) of (2R)-2-[(S)-hydroxy(phenyl)methyl]hex-5-ynoic acid from Step C above in 500 mL of anhydrous acetonitrile at ambient temperature under an atmosphere of nitrogen was added 77.0 mL (513 mmol) of 1,8-diazabicyclo[5.4.0]undec-7-ene 22 mL followed by 66.3 g (440 mmol) of tert-butyldimethylsilyl chloride in three portions over 10 min. The reaction mixture was stirred for 4 h then evaporated in vacuo to remove all volatiles. The residue was diluted with 300 mL of dichloromethane and 100 mL of water. A 1.0 M aqueous hydrogen chloride solution was added to the mixture until a pH of 3 was achieved in the aqueous layer. The phases were separated and the aqueous phase was extracted with dichloromethane (2×100 mL). The combined organics were washed with water (50 mL), brine (50 mL) then dried over magnesium sulfate. After filtration and evaporation in vacuo the residue was dissolved in 350 mL of methanol and 350 mL (280 mmol) of a 0.8 M aqueous potassium carbonate solution was added. The resulting mixture was stirred for 1.5 h then evaporated in vacuo to remove all volatiles. The residue was diluted with 300 mL of dichloromethane and the aqueous phase was acidified with a 5.0 M aqueous hydrogen chloride solution until a pH of 3 was achieved. The phases were separated and the aqueous phase was extracted with dichloromethane (2×100 mL). The combined organics were washed with water (50 mL), brine (50 mL) then dried over magnesium sulfate, filtered and evaporated in vacuo. The residue was purified by silica gel chromatography eluting with a 3-15% ethyl acetate in hexanes gradient to afford the title compound as a colorless solid (42.3 g, 86.6%). $^1$H NMR (500 MHz, CDCl$_3$): δ 7.36-7.27 (m, 5H), 4.78 (d, J=8.7, 1H), 2.90-2.86 (m, 1H), 2.19-2.11 (m, 1H), 2.10-2.03 (m, 1H), 1.90 (t, J=2.6 Hz, 1H), 1.75-1.67 (m, 1H), 1.41-1.34 (m, 1H), 0.83 (s, 9H), 0.02 (s, 3H), −0.27 (s, 3H). LC-MS: m/z (ES) 333.2 (MH)$^+$.

Step E: 4-Methoxybenzyl {(1R)-1-[(R)-{[tert-butyl(dimethyl) silyl]oxy}(phenyl)methyl]pent-4-yn-1-yl}carbamate

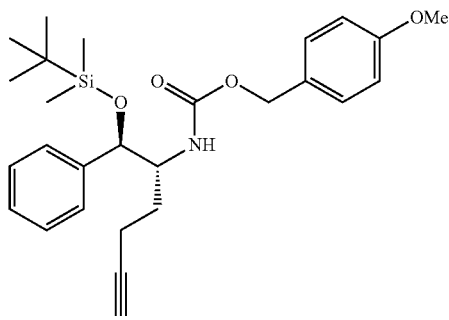 [SMILES: C#CCC[C@@H](NC(=O)OCc1ccc(OC)cc1)[C@H](O[Si](C)(C)C(C)(C)C)c1ccccc1]

To a solution of 40.0 g (120 mmol) of (2R)-2-[(8)-{[tert-butyl(dimethyl)silyl]oxy}(phenyl)methyl]hex-5-ynoic acid from Step D above and 33.5 mL (241 mmol) of triethylamine in 400 mL of anhydrous toluene at ambient temperature under an atmosphere of nitrogen was added 37.5 mL (132 mmol) of diphenylphosphoryl azide. The mixture was stirred for 5 h and then 37.5 mL (301 mmol) of 4-methoxybenzyl alcohol was added. The resulting mixture was heated to 105° C. for 16 h, cooled to ambient temperature and then diluted with 250 mL of a saturated aqueous bicarbonate solution. The phases were separated and the aqueous phase was extracted with ethyl acetate (2×150 mL). The combined organics were washed with water (100 mL), brine (100 mL) then dried over magnesium sulfate, filtered and evaporated in vacuo. The crude residue was purified by silica gel chromatography eluting with 3-10% ethyl acetate in hexanes to afford the title compound as a colorless oil (50.9 g, 90.5%). $^1$H NMR (500 MHz, CDCl$_3$): 7.28-7.21 (m, 7H), 6.87 (d, J=8.4 Hz, 2H), 4.92 (s, 2H), 4.77-4.59 (m, 2H), 3.89-3.84 (m, 1H), 3.81 (s, 3H), 2.30-2.22 (m, 2H), 1.95 (m, 1H), 1.91-1.85 (m, 1H), 1.57-1.50 (m, 1H), 0.89 (s, 9H), 0.06 (s, 3H), −0.15 (s, 3H). LC-MS: m/z (ES) 468.1 (MH)$^+$, 490.0 (MNa)$^+$.

Step F: 4-methoxybenzyl[(1R)-1-[(R)-{[tert-butyl(dimethyl)silyl]oxy}(phenyl)methyl]-5-(4-nitrophenyl)pent-4-yn-1-yl]carbamate

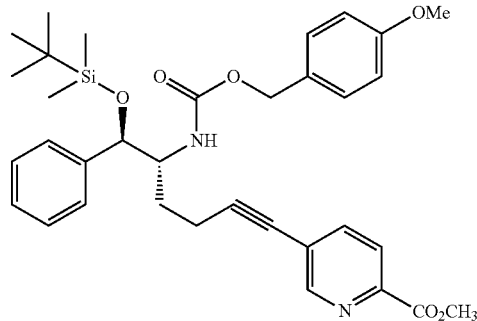 [SMILES: COC(=O)c1ccc(C#CCC[C@@H](NC(=O)OCc2ccc(OC)cc2)[C@H](O[Si](C)(C)C(C)(C)C)c2ccccc2)cn1]

To a solution of acetylene (from Step E, 4 g, 8.00 mmol) and ethyl 5-iodopyridine-2-carboxylate (2.2 g, 8.80 mmol) in anhydrous DMF (50 ml) was added triethylamine (11 mL, 8.00 mmol). Pd(dppf)Cl$_2$ (0.20 g, 0.24 mmol) and copper(I) iodide (100 mg, 0.53 mmol) was added and the mixture degassed with nitrogen (bubble 15 minutes) and the resulting solution heated to 55° C. for 5 hours. The mixture was poured into water (120 mL) and extracted with EtOAc (3×30 mL). The combine organics were then washed with water (2×50 mL), sat. NaCl (20 mL), dried over magnesium sulfate, filtered and evaporated under vacuum. Residue was purified by MPLC (Horizon Biotage 2× Flash 40+) eluting with a gradient of 0-50% ethyl acetate in hexane to give the title compound as a dark red oil (2.10 g, 44%). LC-MS: $C_{34}H_4N_2O_6Si$ calculated 602.28. Found: m/z (ES) 603.3 (MH)$^+$, 625.2 (MNa)$^+$.

Step G: methyl 5-{(5R,6R)-5-amino-6-{[tert-butyl(dimethyl)silyl]oxy}-6-phenylhex-1-yn-1-yl}pyridine-2-carboxylate

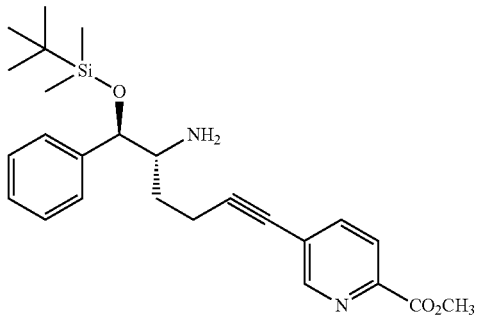 [SMILES: COC(=O)c1ccc(C#CCC[C@@H](N)[C@H](O[Si](C)(C)C(C)(C)C)c2ccccc2)cn1]

To a solution of 4-methoxybenzyl[(1R)-1-[(R)-{[tert-butyl(dimethyl)silyl]oxy}(phenyl)methyl]-5-(4-nitrophenyl)pent-4-yn-1-yl]carbamate (Step F, 2.0 g, 3.32 mmol) in anhydrous dichloromethane (70 mL) was added anhydrous TFA (10 mL, 130 mmol) and the resulting solution stirred for 2 hours at room temperature. The mixture was concentrated under reduced pressure and azeotroped with toluene (2×100 mL). The residues was dissolved in 100 mL dichoromethane and washed with a saturated solution of aqueous sodium bicarbonate (shaken slowly and releasing pressure several times) to remove the TFA. The organic was then washed with water (50 mL) and brine (50 mL), dried over sodium sulfate, filtered, and the filtrate concentrated under vacuum. The crude product (1.40 g, 98%) was used for the next sequence without further purification. LC-MS: $C_{25}H_{34}N_2O_3Si$ calculated 438.26. Found: m/z (ES) 439.3 (MH)$^+$.

Step H: methyl 5-({{(2S,5R)-5-[(R)-([tert-dimethyl)silyl]oxy(phenyl)methyl]pyrrolidin-2-yl}methyl)pyridine-2-carboxylate

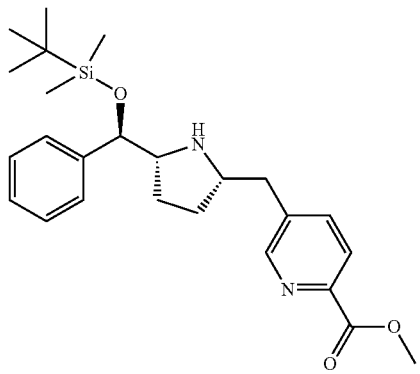 [SMILES: COC(=O)c1ccc(C[C@@H]2CC[C@H]([C@H](O[Si](C)(C)C(C)(C)C)c3ccccc3)N2)cn1]

To a solution of methyl 5-{(5R,6R)-5-amino-6-{[tert-butyl(dimethyl)silyl]oxy}-6-phenylhex-1-yn-1-yl}pyridine-2-carboxylate (1.40 g, 3.20 mmol) in toluene (50 mL) was added palladium acetate (0.08 g, 0.37 mmol) and the mixture degassed with nitrogen (bubble 15 minutes) and the resulting solution heated to 80° C. for 5 hours. The mixture was cooled to room temperature and the solvent removed under vacuum. The residue was then dissolved in methanol (15 mL) and 10% palladium on carbon (400 mg) was added to the solution. The suspension was transferred to a 250 mL Parr shaker flask and was set under hydrogen gas at 50 PSI and vigorously shaken for 16 hours. The gas was expelled and nitrogen was introduced to prevent the possibility of a fire. The catalyst was filtered off through celite and washed with methanol (2×50 mL). The filtrate was then concentrated under reduced pressure and the residue purified via Biotage Flash 40+ (silica gel cartridge) eluting with a gradient of 0-10% methanol in dichloromethane to afford the title compound 810 mg, 56%) as a tan foam. LC-MS: $C_{25}H_{36}N_2O_3Si$ calculated 440.26. Found: m/z (ES) 441.3 (MH)$^+$.

Step J: methyl 5-({{(2S,5R)-1-(tert-butoxycarbonyl)-5-[(R)-{[tert-butyl(dimethyl)silyl]oxy}(phenyl)methyl]pyrrolidin-2-yl}methyl)pyridine-2-carboxylate

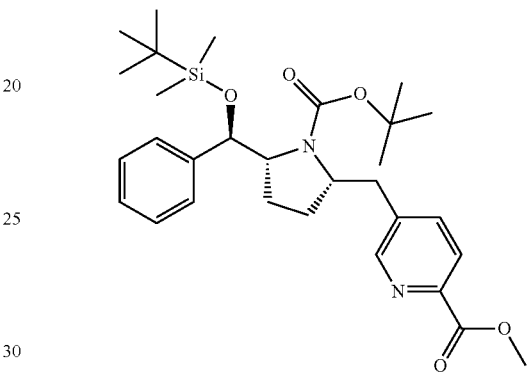

To a solution of methyl 5-({{(2S,5R)-5-[(R)-([tert-dimethyl)silyl]oxy(phenyl)methyl]pyrrolidin-2-yl}methyl)pyridine-2-carboxylate (500 mg, 1.10 mmol) in anhydrous THF (20 mL) was added TEA (0.15 mL, 1.10 mmol) followed by tert-butyl dicarbonate (250 mg, 1.14 mmol) and the resulting mixture stirred overnight at room temperature. The solution was washed with water (20 mL) and extracted with ethyl acetate (40 mL). The organics were combined, dried over sodium sulfate, filtered, and concentrated under reduce pressure. The residue was purified via preparative TLC plate (3×1000 μM) eluting with 30% ethyl acetate in hexane to afford the title compound (475 mg, 78%). LC-MS: $C_{30}H_{44}N_2O_5Si$ calculated 540.38. Found: m/z (ES) 541.3 (MH)$^+$ and 441.3 (M-Boc)$^+$.

Step J: methyl 5-({(2S,5R)-1-(tert-butoxycarbonyl)-5-[(R)-hydroxy(phenyl)methyl]pyrrolidin-2-yl}methyl)pyridine-2-carboxylate

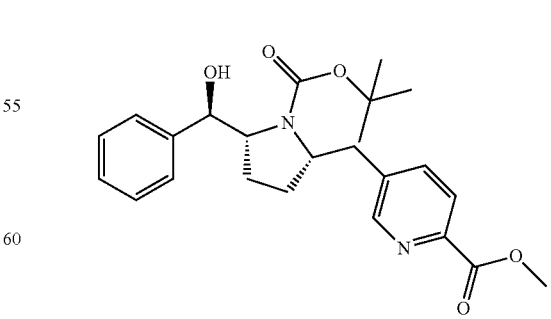

To a solution of methyl 5-({(2S,5R)-1-(tert-butoxycarbonyl)-5-[(R)-{[tert-butyl(dimethyl)silyl]oxy}(phenyl)methyl]pyrrolidin-2-yl}methyl)pyridine-2-carboxylate (475 mg, 0.88 mmol) in THF (2.0 mL) was added 1.0M solution of TBAF in THF (5 mL, 5.0 mmol) and the resulting solution stirred for an 30 minutes at room temperature. The mixture was concentrate under vacuum and the residue taken up in dichloromethane (50 mL). The solution was washed with water (50 mL) and brine (50 mL). The organics were then dried over sodium sulfate, filtered, and concentrated under vacuum. The residue was purified vial preparative TLC plate (2×1000 μM) eluting with 80% ethyl acetate in hexane to afford the title compound as a white foam (334 mg, 89%). LC-MS: $C_{24}H_{30}N_2O_5$ calculated 426.24 found m/z (ES) 427.2 $(MH)^+$ and 327.2 $(M-Boc)^+$.

Step K: 5-({(2S,5R)-1-(tert-butoxycarbonyl)-5-[(R)-hydroxy(phenyl)methyl]pyrrolidin-2-yl}methyl)pyridine-2-carboxylic acid

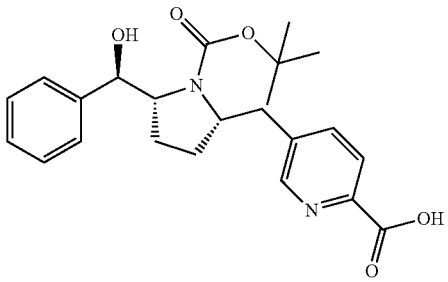 [SMILES: CC(C)(C)OC(=O)N1[C@H](Cc2ccc(C(=O)O)nc2)CC[C@@H]1[C@H](O)c1ccccc1]

To a solution of methyl 5-({(2S,5R)-1-(tert-butoxycarbonyl)-5-[(R)-hydroxy(phenyl)methyl]pyrrolidin-2-yl}methyl)pyridine-2-carboxylate (330 mg, 0.77 mmol) in THF (4 mL) and methanol (4 mL) was added 1N NaOH solution (4 mL, 4.0 mmol) and the resulting solution heated at 60° C. for 1 hour. The mixture was cooled to room temperature and concentrated under reduced pressure to remove the organic solvents. The aqueous layer was adjusted to pH of 6.5 (using 2.0M aqueous HCl) and extracted with ethyl acetate (2×10 mL) and dichloromethane (10 mL). The organics were combined, dried over sodium sulfate, filtered, and concentrated to dryness under vacuum. The product (304 mg, 96%) did not require any further purification and was of reagent grade quality for analog syntheses. LC-MS: $C_{23}H_{28}N_2O_5$ calculated 412.20 found m/z (ES) 413.1 $(MH)^+$ and 313.2 $(M-Boc)^+$.

Intermediate 5

Preparation of [(6S)-4-oxo-4,6,7,8-tetrahydropyrrolo[1,2-a]pyrimidine-6-carboxylic acid (i-5)

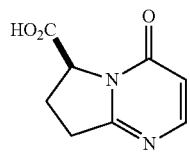 [SMILES: O=C(O)[C@@H]1CCc2nccc(=O)n21]

Step A: Methyl[6(S)-4-oxo-4,6,7,8-tetrahydropyrrolo[1,2-a]pyrimidine-6-carboxylate

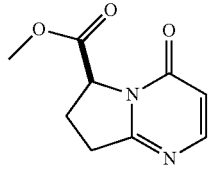

Methyl (2S)-5-methoxy-3,4-dihydro-2H-pyrrole-2-carboxylate (4.19 g, 26.6 mmol) and 3-azatricyclo[4.2.1.0.$^{2,5}$]non-7-en-4-one (2.4 g, 17.8 mmol) was heated at 110° C. overnight. Purification using a Biotage Horizon® system (0-100% ethyl acetate/hexanes mixture) gave the title compound methyl[6(S)-4-oxo-4,6,7,8-tetrahydropyrrolo[1,2-$^\alpha$]pyrimidine-6-carboxylate and intermediate methyl (7S)-9-oxo-3,8-diazatetracyclo[9.2.1.0$^{2,10}$.0$^{4,8}$]tetradeca-3,12-diene-7-carboxylate. The intermediate was heated at 150° C. for 45 minutes to afford the title compound without further purification. LC/MS 195.2 (M+1).

Step B: [(6S)-4-oxo-4,6,7,8-terahydropyrrolo[1,2-a]pyrimidine-6-carboxylic acid

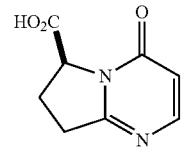 [SMILES: O=C(O)[C@@H]1CCc2nccc(=O)n21]

Methyl[6(S)-4-oxo-4,6,7,8-tetrahydropyrrolo[1,2-a]pyrimidine-6-carboxylate (9.95 g, 51.2 mmol) in tetrahydrofuran (60 mL), methanol (40 mL) and a solution of lithium hydroxide (3.32 g, 77 mmol) in water (40 mL) was stirred at ambient temperature for 1 h. 2 N hydrochloric acid (38.5 mL) was added to neutralize the reaction mixture which was then directly purified by reverse phase HPLC (TMC Pro-Pac C18; 0-40% 0.1% trifluoroacetic acid in acetonitrile/0.1% trifluoroacetic acid in water gradient). The O-alkylation product was eluted fast. The pure fractions were collected and lyophilized overnight afforded the title compound as a pale yellow solid. $^1$H NMR (DMSO-d$_6$): δ 7.89 (d, J=6.6 Hz, 1H), 6.24 (d, J=6.6 Hz, 1H), 4.92 (dd, J=10.0, 3.1 Hz, 1H), 3.12-2.99 (m, 2H), 2.52 (m, 1H), 2.11 (m, 1H). LC/MS 181.2 (M+1).

Intermediate 6

Preparation of [6-oxopyridazin-1(6H)-yl]acetic acid (i-6)

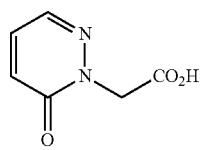 [SMILES: O=C(O)Cn1ncccc1=O]

[3-Chloro-6-oxopyridazin-1(6H)-yl]acetic acid (1.00 g, 5.30 mmol) in methanol (40 mL) was added 100 mg of 10% Pd/C. After the reaction mixture was stirred at ambient temperature under a H$_2$ balloon for 1 h, the Pd was filtered off through celite. The filtrate was concentrated in vacuo and purified by reverse phase HPLC (TMC Pro-Pac C18; 0-40%

0.1% trifluoroacetic acid in acetonitrile/0.1% trifluoroacetic acid in water gradient). Removal of the volatiles in vacuo afforded the title compound as a white crystalline. $^1$H NMR (D$_2$O): δ 8.06 (dd, J=3.9, 1.4 Hz, 1H), 7.56 (dd, J=9.4, 3.9 Hz, 1H), 7.12 (dd, J=9.4, 1.5 Hz, 1H), 4.95 (s, 2H). LC/MS 155.2 (M+1).

Intermediate 7

2-Methyl-5,6-dihydro-4H-cyclopenta[α][1,3]thiazole-4-carboxylic acid (i-7)

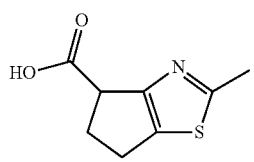

i-7

Step A: Ethyl 2-methyl-5,6-dihydro-4H-cyclopenta[α][1,3]thiazole-4-carboxylate

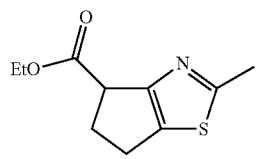

To a solution of ethyl 2-oxocyclopentane-2-carboxylate (56 g, 359 mmol) in chloroform (500 mL) cooled at 0° C. was added bromine (18.5 mL, 359 mmol) over ~20 min. After complete addition mixture allowed to warm to room temperature and stirred overnight Nitrogen gas bubbled through mixture for 90 mins to remove most of HBr. Washed with water (500 mL), sat. NaHCO$_3$ (250 mL), sat. NaCl (200 mL), dried over MgSO$_4$, filtered and evaporated. Residue dissolved in EtOH (500 mL) and thioacetamide (26.9 g, 359 mmol) added, mixture stirred at room temperature for 1 hour then at reflux overnight. The mixture was cooled and evaporated, and the residue partitioned between DCM and sat. NaHCO$_3$, organic layer washed with sat. NaCl, dried over MgSO$_4$, filtered and evaporated. The Residue purified by MPLC (Biotage Horizon: 2×FLASH 65i) eluent: 100% Hexanes (450 mL), gradient rising from 100% Hexanes to 25% EtOAc in Hexanes (1400 mL), then 25% EtOAc in Hexanes to give the title compound (32 g, 42%) as a dark oil. $^1$HNMR (500 MHz, CDCl$_3$) δ: 4.22 (q, J=7.0 Hz, 2H), 3.96 (m, 1H), 3.04 (m, 1H), 2.88 (m, 1H), 2.76 (m, 2H), 2.70 (s, 3H), 1.30 (t, J=7.0 Hz, 3H).

Step B: 2-Methyl-5,6-dihydro-4H-cyclopenta[α][1,3]thiazole-4-carboxylic acid (i-5)

To a solution of 31.5 g (149 mmol) of ethyl 2-methyl-5,6-dihydro-4H-cyclopenta[α][1,3]thiazole-4-carboxylate in THF (450 mL) and methanol (100 mL) (from step A, i-7) was added a solution of lithium hydroxide (149 mL of a 1M solution, 149 mmol) and the resulting mixture stirred at room temperature for 3 hours. Organics removed by evaporation and aqueous residue extracted with Et$_2$O (2×250 mL) and acidified to pH=3 by the addition of 1 M HCl (~170 mL) and saturated with solid NaCl. Extracted with DCM (3×250 mL), combined DCM layers dried over MgSO$_4$, filtered and evaporated. Extracted with DCM (3×250 mL), combined DCM layers dried over MgSO$_4$, filtered and evaporated. Residue triturated with acetonitrile, filtered and dried to give the title compound (7.1 g, 26%) as an off white solid. $^1$HNMR (500 MHz, CDCl$_3$) δ: 11.75 (br s, 1H), 4.02 (m, 1H), 3.00 (m, 1H), 2.90-2.66 (m, 6H).

Intermediates 8 and 9

(4R)-5,6-Dihydro-4H-cyclopenta[d][1,3]thiazole-4-carboxylic acid and (4S)-5,6-dihydro-4H-cyclopenta[d][1,3]thiazole-4-carboxylic acid

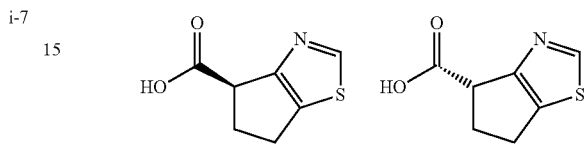

Intermediates 8 and 9 were prepared from ethyl 2-oxocyclopentane carboxylate using a procedure analogous to that used to prepare Intermediate 5. The two enantiomers were separated by SFC CO$_2$S using an AD-H column 10% MeOH/90% CO$_2$, 2.1 ml/min 100 bar 40° C. The first eluting enantiomer, (4S)-5,6-dihydro-4H-cyclopenta[d][1,3]thiazole-4-carboxylic acid, was designated as Intermediate 8 and the second eluting enantiomer, (4R)-5,6-Dihydro-4H-cyclopenta[d][1,3]thiazole-4-carboxylic-acid, was designated as Intermediate 9. $^1$H NMR (500 MHz, CDCl$_3$) δ: 2.59-2.68 (m, 1H), 2.71-2.79 (m, 1H), 2.83-2.90 (m, 1H), 2.92-3.00 (m, 1H), 3.86 (m, 1H), 8.82 (s, 1H), 12.45 (s, 1H).

Intermediate 10

6-(1H-tetrazol-1-yl)-3-azabicyclo[3.1.0]hexane (i-10)

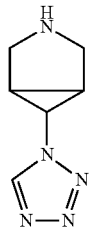

(i-10)

Step A: tert-butyl 6-(1H-tetrazol-1-yl)-3-azabicyclo[3.1.0]hexane-3-carboxylate

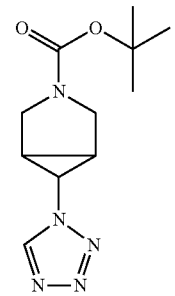 [SMILES: CC(C)(C)OC(=O)N1CC2C(C1)C2n1cnnn1]

To a solution of tert-butyl 6-amino-3-azabicyclo[3.1.0]hexane-3-carboxylate (7.3 g, 25.3 mmol) and triethylorthoformate (24 mL, 152 mmol) in acetic acid (200 mL) was added sodium azide (9.9 g, 152 mmol) and the resulting mixture was set under inert atmosphere. The mixture was heated at 100° C. for 4 h and then cooled to RT at which time the volatiles were removed in vacuo. The residue was taken up in ethyl acetate (200 mL) and washed with aqueous sodium bicarbonate solution, followed by brine. The organics were dried over sodium sulfate, filtered, and concentrate to dryness under vacuum. The residue was placed in the refrigerator overnight and the next day a solid white precipitate was observed. The precipitate was triturated with hexane and the solvent was carefully decanted to give the title compound 3.2 g (50.3%) as a white solid. ESI-MS calculated for $C_{11}H_{17}N_5O_2$: Exact Mass: 251.28. Found 252.28.

Step B: 6-(1H-tetrazol-1-yl)-3-azabicyclo[3.1.0]hexane (i-10)

The title compound from Step A above (2.6 g, 12.2 mmol) was dissolved in 4 M HCl in dioxane (200 mL) and stirred at RT overnight. The product was concentrated under reduced pressure and dried under high vacuum to give 6-(1H-tetrazol-1-yl)-3-azabicyclo[3.1.0]hexane. ESI-MS calculated for $C_6H_9N_5$: Exact Mass: 151.09. Found 152.05.

Intermediate 11 and 12

4-(1-methyl-1H-tetrazol-5-yl)piperidine (i-11) and 4-(2-methyl-2H-tetrazol-5-yl)piperidine (i-12)

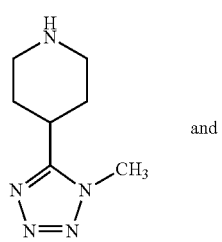

and

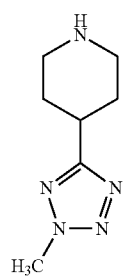

Step A: tert-butyl 4-(1-methyl-1H-tetrazol-5-ylpiperidine-1-carboxylate and tert-butyl 4-(2-methyl-2H-tetrazol-5-yl)piperidine-1-carboxylate

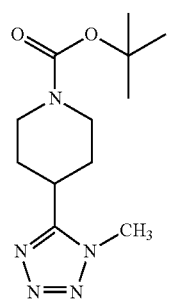 and 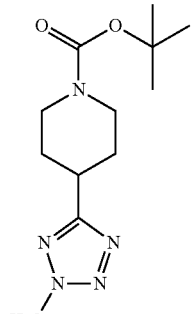

To a solution of tert-butyl 4-(1H-tetrazol-5-yl)piperidine-1-carboxylate (100 mg, 0.4 mmol) and iodomethane (174 μL, 1.2 mmol) in anhydrous DMF (3 ml) was added cesium carbonate (800 mg, 2.4 mmol) and the resulting mixture heated to 80° C. for 2 h. After allowing to cool to RT, the mixture was poured into water and extracted with ethyl acetate (3×10 mL). The organics were combined, dried over magnesium sulfate, filtered and concentrated under reduced pressure. The residue was purified via preparative TLC plate (1000 μM) eluting with 80% ethyl acetate in hexane which also separate the two isomers. The isomers were labeled as isomer 1 and isomer 2 in the order that they eluted off the plate. Isomer 1 (45 mg, 25%) was identified as the Boc-4-(1-methyl-1H-tetrazol-5-yl)piperidine and the other (isomer 2, 30 mg, 16%) to be the 2-methyl substituted tetrazole.

Isomer 1: ESI-MS calculated for $C_{12}H_{23}N_5O_2$: Exact Mass: 267.13. Found 268.12.

Isomer 2: ESI-MS calculated for $C_{12}H_{23}N_5O_2$: Exact Mass: 267.13. Found 268.12.

Step B: 4-(1-methyl-1H-tetrazol-5-yl)piperidine (i-11)

The isomer 1 from Step A above (45 mg, 0.16 mmol) was dissolved in 4 M HCl in dioxane (1.0 mL) and stirred at RT for 1 h. The product was concentrated under reduced pressure and dried under high vacuum to give the title compound (i-11) (25 mg, 95%). ESI-MS calculated for $C_7H_{15}N_5$: Exact Mass: 167.13. Found 168.12.

Step C: 4-(2-methyl-2H-tetrazol-5-yl)piperidine (i-12)

The title compound (i-12) was prepared according to the procedure outlined above in Step B replacing the isomer 1 with the isomer 2 from Step A above.

ESI-MS calculated for both is $C_9H_{17}N_5$: Exact Mass: 167.13. Found 168.12.

Intermediate 13 tert-butyl (1R,5S,6r)-6-(1,3,4-oxadiazol-2-yl)-3-azabicyclo[3.1.0]hexane-3-carboxylate (i-13)

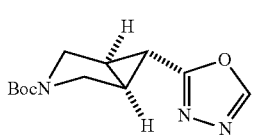

Step A: tert-butyl (1R,5S,6r)-6-(hydrazinocarbonyl)-3-azabicyclo[3.1.0]hexane-3-carboxylate

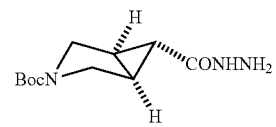

To a solution of 4.50 g (19.8 mmol) (1R,5S,6r)-3-(tert-butoxycarbonyl)-3-azabicyclo[3.1.0]hexane-6-carboxylic acid in 50 ml anhydrous tetrahydrofuran at −10° C. was added 3.04 ml (21.8 mmol) triethylamine followed by 2.08 ml (21.8 mmol) ethyl chloroformate slowly. The reaction was stirred between −20° C. to −10° C. for 20 min. The solid was filtered off and rinsed with tetrahydrofuran. The tetrahydrofuran filtrate was added into 1.04 ml (33.4 mmol) hydrazine hydrate in 50 ml anhydrous methanol at 0° C. The reaction was stirred at ambient temperature for 2 h. The crude product was concentrated and purified by using a Biotage Horizon® system (0-10% ethyl acetate/methanol with 10% ammonia) to give 3.0 g (75%) of the title compound as white solid. $^1$H NMR (CDCl$_3$): δ 3.67 (d, J=11.2 Hz, 1H), δ 3.65 (d, J=10.8 Hz, 1H), δ 3.42 (d, J=10.7 Hz, 2H), δ 2.09 (s, 2H), δ 1.43 (s, 9H), δ 1.31 (m, 1H).

Step B: tert-butyl (1R,5S,6r)-6-(1,3,4-oxadiazol-2-yl)-3-azabicyclo[3.1.0]hexane-3-carboxylate (i-13)

0.10 g (0.40 mmol) of the title compound from Step A above in 2.0 ml (12 mmol) triethyl orthoformate was added to 0.024 ml acetic acid. The solution was heated at 110° C. for 24 h. The crude product was concentrated and purified using a Biotage Horizon® system (0-60% ethyl acetate/hexanes mixture) to give 52 mg 50% of the title compound (i-13) as colorless oil. $^1$H NMR (CDCl$_3$): δ 8.26 (s, 1H), δ 3.72 (d, J=11.0 Hz, 1H), δ 3.65 (d, J=11.0 Hz, 1H), δ 3.40 (d, J=11.3 Hz, 2H), δ 2.15 (s, 2H), δ 1.97 (t, J=3.6 Hz, 1H), δ 1.37 (s, 9H)

Intermediate 14 tert-butyl (1R,5S,6r)-6-(2H-tetrazol-5-yl)-3-azabicyclo[3.1.0]hexane-3-carboxylate (i-14)

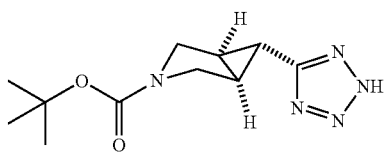

(i-14)

To a solution of 0.15 g (0.70 mmol) of tert-butyl (1R,5S,6r)-6-cyano-3-azabicyclo[3.1.0]hexane-3-carboxylate 3 mL of DMF was added 0.14 g (2.1 mmol) of sodium azide and 0.11 g (2.1 mmol) of ammonia chloride. Then the mixture was stirred at 100° C. overnight LC-MS showed the desired product formed. The mixture was diluted with ethyl acetate (50 mL), washed with aqueous sodium hydrogen carbonate (saturated, 3×25 mL) and brine, dried with sodium sulfate, filtered and the solvent was evaporated under reduced pressure. The residue was purified by column chromatography on silica gel Biotage 40S, eluting with dichloromethane/methanol to afford the title compound as a colorless solid (0.12 g, 70%). LC-MS: m/z (ES) 252.1 (MH)$^+$.

Intermediates 15 and 16 tert-butyl (1R,5S,6r)-6-(1-methyl-1H-tetrazol-5-yl)-3-azabicyclo[3.1.0]hexane-3-carboxylate (i-15) and tert-butyl (1R,5S,6r)-6-(2-methyl-2H-tetrazol-5-yl-3-azabicyclo[3.1.0]hexane-3-carboxylate (i-16)

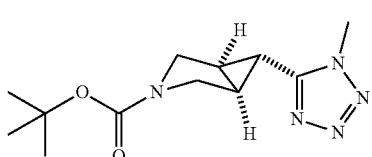

i-15

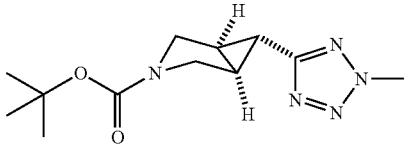

i-16

To a solution of 0.12 g (0.15 mmol) of tert-butyl (1R,5S,6r)-6-(2H-tetrazol-5-yl)-3-azabicyclo[3.1.0]hexane-3-carboxylate and 0.10 g (0.75 mmol) of potassium carbonate in 3 mL of DMF was added 0.019 ml (0.30 mmol) of MeI. Then the mixture was stirred at RT for overnight. LC-MS showed the desired product formed. The mixture was diluted with ethyl acetate (50 mL), washed with aqueous sodium hydrogen carbonate (saturated, 3×25 mL) and brine, dried with sodium sulfate, filtered and the solvent was evaporated under reduced pressure. The residue was purified by column chromatography on silica gel Biotage 12S, eluting with EtOAc/hexane to afford the title compounds higher Rf: tert-butyl (1R,5S,6r)-6-(2-methyl-2H-tetrazol-5-yl)-3-azabicyclo[3.1.0]hexane-3-carboxylate (i-16) as a colorless solid (0.021 g, 53%). LC-MS: m/z (ES) 266.1 (MH)$^+$. $^1$H-NMR (500 MHz, CDCl$_3$) δ 4.25 (s, 3H), 3.80 (d, J=11 Hz, 1H), 3.70 (d, J=11 Hz, 1H), 3.46 (m, 2H), 2.12 (d, J=11 Hz, 2H), 2.01 (s, 1H), 1.43 (s, 9H). Lower Rf: tert-butyl (1R,5S,6r)-6-(1-methyl-1H-tetrazol-5-yl)-3-azabicyclo[3.1.0]hexane-3-carboxylate (i-15) as a colorless solid (0.01 g, 25%). LC-MS: m/z (ES) 266.1 (MH)$^+$. $^1$H-NMR (500 MHz, CDCl$_3$) δ 4.05 (s, 3H), 3.82 (d, J=11 Hz, 1H), 3.75 (d, J=11 Hz, 1H), 3.55 (m, 2H), 2.35 (s, 1H), 2.25 (s, 1H), 1.75 (s, 1H), 1.45 (s, 9H).

Intermediate 17

1-(pyridine-2-ylmethyl)piperazine (i-17)

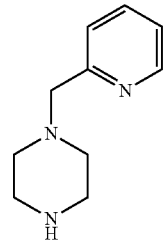

(i-17)

Step A: Tert-butyl 4-(pyridine-2-ylmethyl)piperazine-1-carboxylate

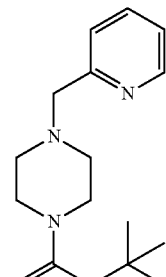

To a stirred suspension of 0.28 g (0.71 mmol) of sodium hydride (60% mineral oil dispersion) in 5 mL anhydrous N,N-dimethylformamide at 0° C. was added 0.12 g (0.65 mmol) tert-butyl 1-piperazine-carboxylate. The resulting mixture was stirred under an atmosphere of nitrogen for 15 min and then allowed to warm to ambient temperature at which point 0.14 g (0.59 mmol) of 2-(bromomethyl)pyridine was added. After 4 h, quench the reaction with 25 mL cold water and extract the resulting solution with 25 mL ethyl acetate. The organic layer was washed with water (2×25 mL), dried over magnesium sulfate, filtered and evaporated in vacuo to afford the title compound which was purified by reverse-phase HPLC (TMC Pro-Pac C18; 10-100% 0.1% trifluoroacetic acid in acetonitrile/0.1% trifluoroacetic acid in water gradient). LC/MS: m/z (ES) 278.1 (MH)$^+$.

Step B: 1-(pyridine-2-ylmethyl)piperazine

A solution of 0.11 g (0.4 mmol) of the title compound from Step A above in 1 mL dichloromethane and 1 mL trifluoroacetic acid was stirred at ambient temperature for 1 h. All volatiles were removed in vacuo and the crude light brown residue was carried forward without purification. LC/MS: m/z (ES) 178.2 (MH)$^+$.

Intermediate 18

Tert-butyl 4-(1H-tetrazol-5-ylmethylpiperazine-1-carboxylate (i-18)

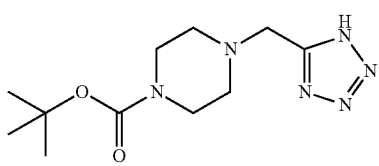

(i-18)

Step A: Tert-butyl 4-(cyanomethyl)piperazine-1-carboxylate

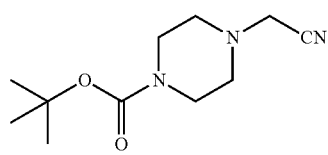 [SMILES: CC(C)(C)OC(=O)N1CCN(CC#N)CC1]

To a stirred solution of 2.7 g (15 mmol) of tert-butyl piperazine-1-carboxylate in 30 mL of anhydrous N,N-dimethylformamide was added 2.4 g (17 mmol) of potassium carbonate followed by 2.1 g (17 mmol) of bromoacetonitrile. The resulting heterogeneous mixture was stirred at ambient temperature of 12 h, quenched with water then extracted with ethyl acetate. The combined organic layers were washed with water then brine, dried over magnesium sulfate and evaporated to dryness in vacuo. The residue was purified by silica gel chromatography eluting with a 0-75% acetone in hexanes gradient to afford the title compound as clear gum (1.0 g, 30%). $^1$H-NMR (500 MHz, CDCl$_3$) δ 3.53 (s, 2H), 3.48 (t, J=5.0 Hz, 4H), 2.53 (t, J=5.0 Hz, 4H), 1.45 (s, 9H). LC-MS: m/z (ES) 226.2 (MH)$^+$.

Step B: Tert-butyl 4-(1H-tetrazol-5-ylmethyl)piperazine-1-carboxylate (i-18)

To a stirred suspension of 1.50 g (6.66 mmol) of the title compound from Step A above in 25 mL of anhydrous toluene was added 1.38 g (10.0 mol) of triethylamine hydrochloride followed by 0.65 g (10 mmol) of sodium azide. The resulting mixture was heated to 80° C. for 12 h then cooled to ambient temperature. All volatiles were removed in vacuo, and the residue suspended in 5 mL of brine and 1.0 N aqueous hydrogen chloride solution was added until pH of ~4 was achieved. The aqueous phase was extracted with chloroform and the combined organics were dried over magnesium sulfate and evaporated to dryness in vacuo. The residue was purified by silica gel chromatography eluting with a 0-100% acetone in hexanes gradient to afford the title compound (i-18) as white solid (1.1 g, 63%). $^1$H-NMR (500 MHz, DMSO-d) δ 3.82 (s, 2H), 3.29 (br s, 4H), 2.38-2.34 (m, 4H), 1.36 (s, 9H). LC-MS: m/z (ES) 269.0 (MH)$^+$.

Intermediate 19

1-(1H-Tetrazol-5-ylmethyl)piperazine, bis(trifluoroacetic acid) salt (i-19)

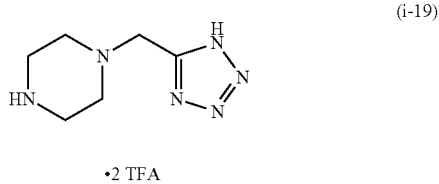 [SMILES: C1CN(Cc2nnn[nH]2)CCN1]

(i-19)

•2 TFA

To a stirred solution of 0.050 g (0.19 mmol) of Intermediate i-18 in 3 mL of dichloromethane was added 1 mL of trifluoroacetic acid and the resulting mixture was stirred for 1 h. All volatiles were removed in vacuo and the pale yellow residue was suspended in toluene. All volatiles were then removed in vacuo and this process was repeated two additional times. The pale yellow residue that was obtained was dried under high vacuum overnight to afford the title compound as a yellow gum (0.072 g, 98%). LC-MS: m/z (ES) 169.0 (MH)$^+$.

EXAMPLE 1

(4R)—N-[5-((2S,5R)-5-[(R)-hydroxy(phenyl)methyl]pyrrolidin-2-yl)methyl)pyridin-2-yl]-5,6-dihydro-4H-cyclopenta[d][1.3]thiazole-4-carboxamide

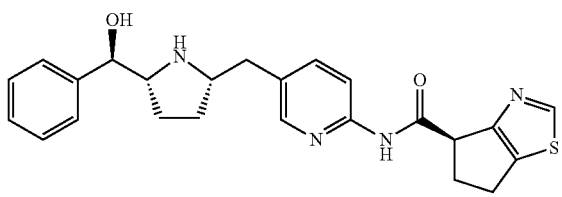 [SMILES: O=C(Nc1ccc(C[C@@H]2CC[C@H]([C@H](O)c3ccccc3)N2)cn1)[C@@H]1CCc2scnc21]

Step A: Tert-butyl-(2S,5R)-2-[(6-{[(4R)-5,6-dihydro-4H-cyclopenta[d][1,3]thiazol-4-ylcarbonyl]amino}pyridin-3-yl}methyl]-5-[(R)-hydroxy(phenyl)methyl]pyrrolidine-1-carboxylate

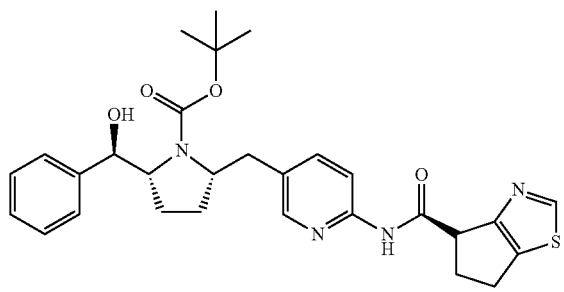

To a solution of 20 mg (0.058 mmol) of tert-butyl (2S,5R)-2-[(6-aminopyridinyl-3-yl)methyl]-5-[(R)-hydroxy(phenyl)methyl]pyrrolidine-1-carboxylate (i-3) and 16.5 mg (0.058 mmol) of (4R)-5,6-Dihydro-4H-cyclopenta[d][1,3]thiazole-4-carboxylic acid (i-9) in anhydrous DMF (1 mL) was added EDC (16.5 mg, 0.086 mL), HOBt (13.2 mg, 0.086 mmol) and Hunig's Base (0.03 mL, 0.17 mmol) and the resulting mixture stirred at room temperature overnight Poured into water (5 mL) and extracted with EtOAc (3×5 mL), combined EtOAc layers washed with water (2×5 mL), sat. NaCl (5 mL), dried over $MgSO_4$, filtered and evaporated. Residue purified by preparative TLC plate (1000 μM silica) to give the title compound (26.3 mg, 70%).

Step B: (4R)—N-[5-{((2S,5R)-5-[(R)-hydroxy(phenyl)methyl]pyrrolidin-2-yl)methyl)pyridin-2-yl]-5,6-dihydro-4H-cyclopenta[d][1,3]thiazole-4-arboxamide

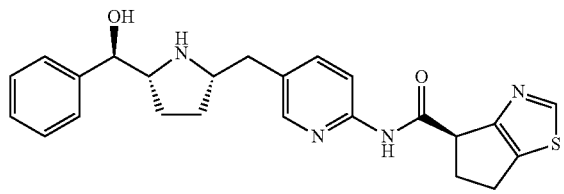 [SMILES: O=C(Nc1ccc(C[C@@H]2CC[C@H]([C@H](O)c3ccccc3)N2)cn1)[C@@H]1CCc2scnc21]

To a solution of 26 mg (0.04 mmol) of tert-butyl-(2S,5R)-2-[(6-{[(4R)-5,6-dihydro-4H-cyclopenta[d][1,3]thiazol-4-ylcarbonyl]amino}pyridin-3-yl}methyl]-5-[(R)-hydroxy(phenyl)methyl]pyrrolidine-1-carboxylate (from step A, Example 1) in DCM (2 mL) was added trifluoroacetic acid (1.0 mL, 13 mmol) and the resulting mixture stirred at room temperature for 4 hours. The mixture was evaporated and passed through an SCX cartridge eluting with 2 M $NH_3$ in methanol to free up the base. Product purified by PREP-TLC 2× [20×20 cm×1000 micron] eluent: 10% MeOH in DCM+ 1% $NH_4OH$ and product lyophilized to give (13 mg, 75%) as a white fluffy solid. m/z (ES) 435 $(MH)^+$. $^1HNMR$ (500 MHz, DMSO-d6) δ:

Using the Biological Assays ($β_3$AR-cAMP) as described above, the human β3 functional activity of Example 1 was determined to be between 20.4 nM.

EXAMPLES 2-4

Using procedures similar to those described above, Examples 2-4 were prepared from the appropriate starting materials.

Using the Biological Assays (β3AR-cAMP) as described above, the human β3 functional activity of each compound was determined. The human β3 binding activities of Examples 2-4 are represented as the following ranges in Table 1:

less than 10 nM (+);

11-100 nM (++);

101-1000 nM (+++); and greater than 1000 nM but less than 3000 nM (++++).

TABLE 1

| Example Number | Chemical Name | R | MW | MS (ES) $(MH)^+$ | Human β3 Binding |
|---|---|---|---|---|---|
| 2 | N-[5-({(2S, 5R)-5-[(R)-hydroxy(phenyl)methyl]pyrrolidin-2-yl}methyl)pyridin-2-yl]-4-oxo-4,6,7,8-tetrahydropyrrolo[1,2-a]pyrimidine-6-carboxamide | | 445.52 | 446.54 | ++ |

TABLE 1-continued

| Example Number | Chemical Name | R | MW | MS (ES) (MH)+ | Human β3 Binding |
|---|---|---|---|---|---|
| 3 | N-[5-({(2S, 5R)-5-[(R)-hydroxy(phenyl)methyl]pyrrolidin-2-yl}methyl)pyridin-2-yl]-2-(6-oxopyridazin-1(6H)-yl)acetamide | | 419.49 | 420.24 | +++ |
| 4 | N-[5-([(2S, 5R)-5-[(R)-hydroxy(phenyl)methyl]pyrrolidin-2-yl]methyl)pyridin-2-yl]-2-(5-phenyl-4H-1,2,4-triazol-3-yl)acetamide | | 468.58 | 469.52 | ++ |

EXAMPLE 5

(R)-Phenyl-(2R,5S)-5-{[6-({4-[1-(2,2,2-trifluoroethyl)-1H-tetrazol-5-yl]piperidin-1-yl}carbonyl-pyridin-3-yl]methyl}pyrrolidin-2-yl)methanol

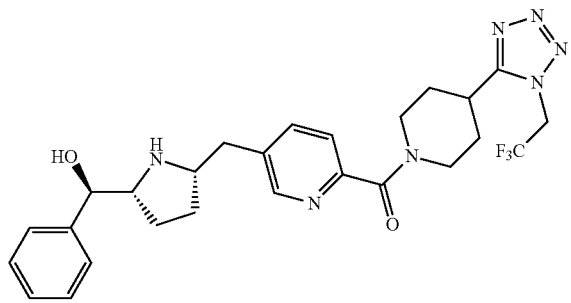 [SMILES: O=C(c1ccc(C[C@@H]2CC[C@H]([C@H](O)c3ccccc3)N2)cn1)N1CCC(c2nnnn2CC(F)(F)F)CC1]

Step A: Tert-butyl (2R,5S)-2-[(R)-hydroxy(phenyl)methyl]-5-{[6-({4-[(1-(2,2,2-trifluoroethyl)-1H-tetrazol-5-yl]piperidin-1-yl}carbonyl)pyridin-3-yl]methyl}pyrrolidine-1-carboxylate

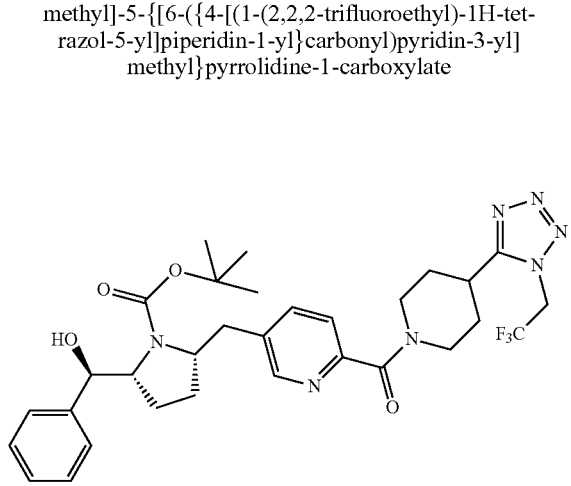

To a solution of 4-{((2S,5R)-1-(tert-butoxycarbonyl)-5-[(R)-hydroxy(phenyl)methyl]pyrrolidin-2-yl)methyl}benzoic acid (82 mg, 0.2 mmol) (i-4) and 4-(1H-pyrazol-1-yl)piperidine (30 mg, 0.2 mmol) in 1.5 mL anhydrous DMF was added a 0.5 M solution of HOAt in DMF (0.4 mL, 0.2 mmol) followed by EDC (78 mg, 0.4 mmol) and DIEA (70 μL, 0.4 mmol). The resulting mixture was stirred at RT under nitrogen atmosphere for 16 h. The mixture was washed with water and extracted with dichloromethane (2×5 mL). The organics were combined, dried over sodium sulfate, filtered and concentrated in vacuum. The residue was purified by preparative TLC plate (1000 uM) eluting with 5% MeOH in dichloromethane to afford the title compound (88 mg, 81%). ESI-MS calculated for $C_{32}H_{40}N_4O_4$: Exact Mass: 544.30. Found 545.30 (MH)+ and 567.28 (MNa)+.

Step B: (R)-phenyl-(2R,5S)-5-{[6-({4-[1-(2,2,2-trifluoroethyl)-1H-tetrazol-5-yl]piperidin-1-yl}carbonyl)pyridin-3-yl]methyl}pyrrolidin-2-yl)methanol

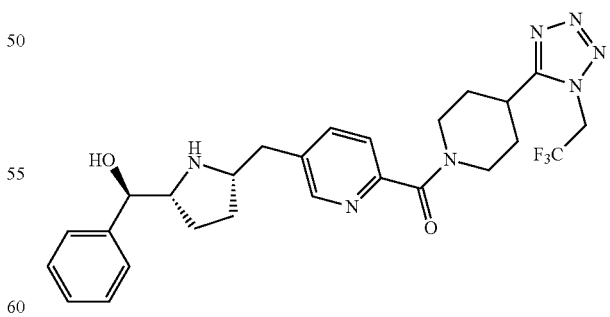

The title compound from Step A above (85 mg, 0.16 mmol) was dissolved in 4 M HCl in dioxane plus 10% water (v/v) (2 mL) and stirred at RT for 2 h. The product was concentrated under reduced pressure and dried under high vacuum to give the title compound. ESI-MS calculated for $C_{27}H_{32}N_4O_2$: Exact Mass: 444.25. Found 445.24.

Using the Biological Assays as described above, the human β3 functional activity was determined to be between 101 to 1000 nM.

EXAMPLE 6

(R)-phenyl[(2R,5S)-5-[(6-{[(1R,5S,6S)-6-(1H-tetrazol-1-yl)-3-azabicyclo[3.1.0]hex-3yl]carbonyl}pyridin-3-yl)methyl]pyrrolidine-2-yl]methanol

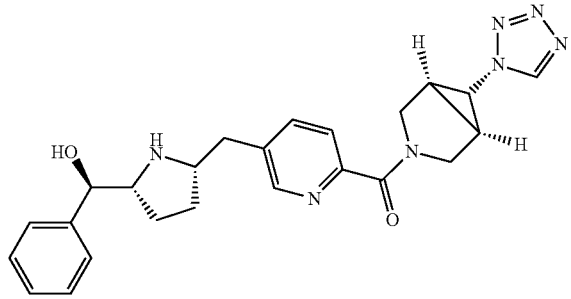

Step A: Tert-butyl (2R,5S)-2-[(R)-hydroxy(phenyl)methyl]-5-[(6-{[(1R,5S,6S)-6-(1H-tetrazol-yl)-3-azabicyclo[3.1.0]hex-3-yl]carbonyl}pyridin-3-yl)methyl]pyrrolidine-1-carboxylate

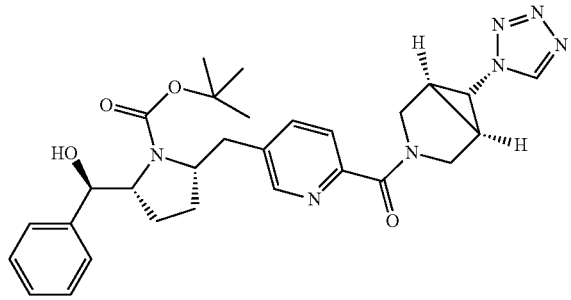

To a solution of 5-{((2S,5R)-1-(tert-butoxycarbonyl)-5-[(R)-hydroxy(phenyl)methyl]pyrrolidin-2-yl)methyl}pyridine-2-carboxylic acid (i-4, 30 mg, 0.0685 mmol) and 6-(1H-tetrazol-1-yl)-3-azabicyclo[3.1.0]hexane (13 mg, 0.0685 mmol) in 1.5 mL anhydrous DMF was added HATU (26 mg, 0.065 mmol) followed by TEA (0.02 mL, 0.21 mmol). The resulting mixture was stirred at RT under nitrogen atmosphere for 3 h. The mixture was washed with water and extracted with ethyl acetate (2×5 mL). The organics were washed with brine, separated, dried over sodium sulfate, filtered and concentrated under vacuum. The residue was purified by preparative TLC plate (1000 uM) eluting with 5% MeOH in dichloromethane to afford the title compound (27.6 mg, 74%). ESI-MS calculated for $C_{29}H_{35}N_7O_4$: Exact Mass: 545.64. Found 546.64 (MH)$^+$ and 568.64(MNa)$^+$.

Step B: ((R-phenyl[(2R,5S)-5-[(6-{[(1R,5S,6s)-(1H-tetrazol-1-yl)-3-azabicyclo[3.1.0]hex-3yl]carbonyl}pyridin-3-yl)methyl]pyrrolidine-2-yl]methanol

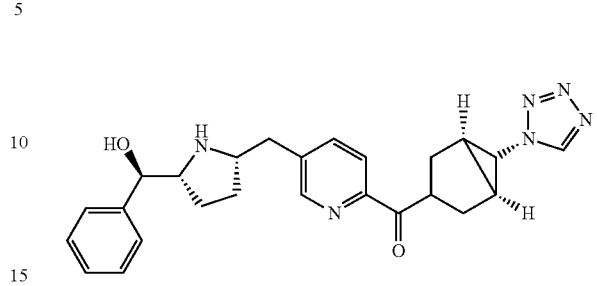

To a solution of the title compound from Step A above (27.6 mg, 0.050 mmol) in dichloromethane (2 mL) was added TFA (1.0 mL) and the resulting solution stirred at RT for 2 hours. The volatiles were removed under vacuum and the residue dissolved in ethyl acetate (10 mL). The solution was washed with sodium bicarbonate (5 mL), dried over sodium sulfate, filtered, and then concentrated to dryness under vacuum to afford the title compound (13.7 mg, 62%) as its free base form. ESI-MS calculated for $C_{24}H_{27}N_7O_2$: Exact Mass: 445.53. Found 446.54.

Using the Biological Assays as described above, the human β3 functional activity was determined to be between 11 to 100 nM.

EXAMPLE 7

(R)-phenyl[(2R,5S)-5-[(6-{[4-(pyridin-2-ylmethyl)piperazin-1-yl]carbonyl}pyridin-3-yl)methyl]pyrrolidin-2-yl]methanol

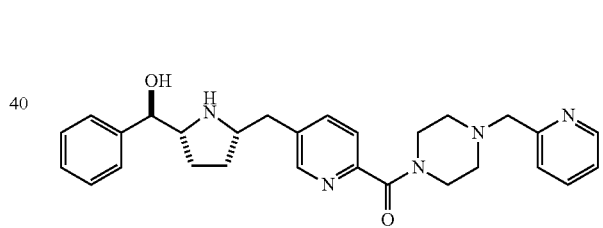

Step A: Tert-butyl (2R,5S)-2-[(R)-hydroxy(phenyl)methyl]-5-[(6-{[4-(pyridin-2-ylmethyl)piperazin-1-yl]carbonyl}pyridin-3-yl)methyl]pyrrolidine-1-carboxylate

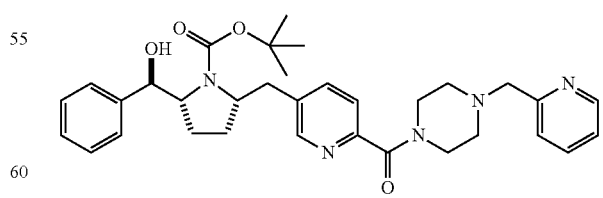

To a solution of 0.018 g (0.102 mmol) of (1-(pyridine-2-ylmethyl)piperazine and 0.035 g (0.085 mmol) of 5-{((2S,5R)-1-(tert-butoxycarbonyl)-5-[(R)-hydroxy(phenyl)methyl]pyrrolidin-2-yl)methyl}pyridine-2-carboxylic acid in 2 mL of N,N-dimethylformamide was added 0.074 mL (0.425 mmol) of N,N-diisopropylethylamine and 0.065 g (0.170 mmol) of HATU. The resulting mixture was stirred under an atmosphere of nitrogen for 3 h and then purified directly by reverse-phase HPLC (TMC Pro-Pac C18; 10-100% 0.1% trifluoroacetic acid in acetonitrile/0.1% trifluoroacetic acid in water gradient).

LCMS: for $C_{33}H_{41}N_5O_4$: Exact Mass: 571.53. Found 572.5 (MH)$^+$.

Step B: (R)-phenyl[(2R,5S)-5-[(6-{[4-(pyridin-2-ylmethyl)piperazin-1-yl]carbonyl}pyridin-3-yl)methyl]pyrrolidin-2-yl]methanol

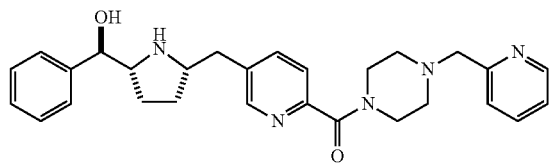

A solution of 0.038 g (0.067 mmol) of the title compound from Step A above in 1 mL dichloromethane and 1 mL trifluoroacetic acid was stirred at ambient temperature for 1 h. All volatiles were removed in vacuo and the crude light brown residue was purified directly by reverse-phase HPLC to afford the title compound (TMC Pro-Pac C18; 10-100% 0.1% trifluoroacetic acid in acetonitrile/0.1% trifluoroacetic acid in water gradient). $^1$H-NMR (500 MHz, CD$_4$O)

Using the Beta-3 agonist in vitro functional assay described above the human Beta-3 agonist functional activity of this Example was determined to be between 101 to 1000 nM.

EXAMPLES 8-14

Using procedures similar to those described above, Examples 8-14 were prepared from the appropriate starting materials.

Using the Beta-3 agonist in vitro functional assay described above the human Beta-3 agonist functional activity of each compound was determined and shown in Table 2 as the following ranges:
less than 10 nM (+);
11-100 nM (++);
101-1000 nM (+++); and
greater than 1001 nM but less than 3000 nM (++++).

TABLE 2

| Example Number | Chemical Name | R | MW | MS (MH)$^+$ | Human β3 Agonist Functional Activity |
|---|---|---|---|---|---|
| 8 | 8-{[5-({(2S, 5R)-5-[(R)-hydroxy(phenyl)methyl]pyrrolidin-2-yl}methyl)pyridin-2-yl]carbonyl}-2-oxa-8-azaspiro[4.5]decan-1-one | | 449.6 | 450.4 | ++ |
| 9 | (R)-{(2R, 5S)-5-[(6-{[6-(1-methyl-1H-tetrazol-5-yl)-3-azabicyclo[3.1.0]hex-3-yl]carbonyl}pyridin-3-yl)methyl]pyrrolidin-2-yl}(phenyl)methanol | | 459.5 | 460.3 | ++ |
| 10 | (R)-{(2R, 5S)-5-[(6-{[6-(2,2,2-trifluoroethyl)-1H-tetrazol-5-yl)-3-azabicyclo[3.1.0]hex-3-yl]carbonyl}pyridin-3-yl)methyl]pyrrolidin-2-yl}(phenyl)methanol | | 527.5 | 528.4 | ++ |

TABLE 2-continued

| Example Number | Chemical Name | R | MW | MS (MH)+ | Human β3 Agonist Functional Activity |
|---|---|---|---|---|---|
| 11 | (R)-{(2R, 5S)-5-[(6-{[6-(1,3,4-oxadiazol-2-yl)-3-azabicyclo[3.1.0]hex-3-yl]carbonyl}pyridin-3-yl)methyl]pyrrolidin-2-yl)(phenyl)methanol | | 445.5 | 446.4 | ++ |
| 12 | (R)-{(2R, 5S)-5-[(6-{[6-(5-ethyl-1,3,4-oxadiazol-2-yl)-3-azabicyclo[3.1.0]hex-3-yl]carbonyl}pyridin-3-yl)methyl]pyrrolidin-2-yl)(phenyl)methanol | | 473.5 | 474.5 | ++ |
| 13 | (R)-phenyl{(2R, 5S)-5-[(6-{[6-(5-pyrazin-2-yl-1,3,4-oxadiazol-2-yl)-3-azabicyclo[3.1.0]hex-3-yl]carbonyl}pyridin-3-yl)methyl]pyrrolidin-2-yl}methanol | | 523.6 | 524.4 | + |
| 14 | (R)-phenyl[(2R, 5S)-5-({6-[(4-{[2-(2,2,2-trifluoroethyl)-2H-tetrazol-5-yl]methyl}piperazin-1-yl)carbonyl]pyridin-3-yl}methyl)pyrrolidin-2-yl]methanol | | 544.6 | 545.4 | ++ |

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the active agents used in the instant invention as indicated above. Likewise, the specific pharmacological responses observed may vary according to and depending upon the particular active compound selected or whether there are present pharmaceutical carriers, as well as the type of formulation employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of Formula Ia, or a pharmaceutically acceptable salt thereof, or a stereoisomer thereof, or a pharmaceutically acceptable salt of the stereoisomer thereof:

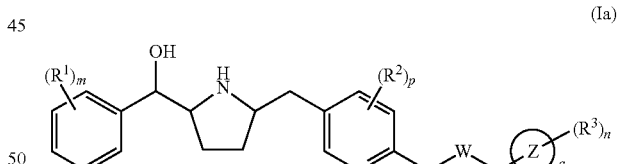

(Ia)

wherein
m is 0, 1, 2, or 3;
n is 0, 1, 2, 3, or 4;
p is 0, 1, or 2;
q is 0 or 1;
X is selected from the group consisting of:
 (1) a bond,
 (2) $C_1$-$C_4$ alkanediyl, $C_2$-$C_4$ alkenediyl, and $C_2$-$C_4$ alkynediyl, wherein each of alkanediyl, alkenediyl and alkynediyl is optionally substituted with 1 to 3 groups independently selected from (a) halogen, and (b) —OR$^a$, and
 (3) absent;
or V is a carbonyl group and W is 3-azabicyclo[3.1.0]hex-3-yl;

Z is tetrazolyl;
each occurrence of $R^1$ is independently selected from the group consisting of:
  (1) $C_1$-$C_4$ alkyl optionally substituted with 1 to 3 halogen atoms, and
  (2) halogen;
each occurrence of $R^2$ is independently selected from the group consisting of:
  (1) halogen, and
  (2) methyl;
each occurrence of $R^3$ is independently selected from the group consisting of:
  (1) halogen,
  (2) —$OR^a$,
  (3) oxo,
  (4) —$CO_2R^a$, and
  (5) $C_1$-$C_4$ alkyl optionally substituted with 1 to 3 groups independently selected from halogen, —$OR^a$, and —$CO_2R^a$;
each occurrence of $R^a$ is independently selected from the group consisting of:
  (1) hydrogen, and
  (2) $C_1$-$C_4$ alkyl optionally substituted with 1 to 3 halogen atoms; and
each occurrence of $R^b$ is independently selected from the group consisting of:
  (1) hydrogen, and
  (2) $C_1$-$C_4$ alkyl optionally substituted with 1 to 3 groups independently selected from the group consisting of:
    (a) hydroxy, and
    (b) halogen.

2. The compound of claim 1, wherein m is 0, n is 0, 1, 2, or 3, and p is 0, and wherein each occurrence of $R^3$ is independently selected from the group consisting of:
  (1) halogen,
  (2) —OH,
  (3) oxo,
  (4) —$CO_2H$,
  (5) methyl optionally substituted with 1 to 3 groups selected from halogen, and hydroxyl, and
  (6) ethyl optionally substituted with 1 to 3 groups selected from halogen, and hydroxyl.

3. The compound of claim 1 having Formula (Ib) or a pharmaceutically acceptable salt thereof:

(Ib)

wherein
n is 0, 1, 2 or 3;
q is 0 or 1;
X is selected from the group consisting of:
  (1) a bond,
  (2) $C_1$-$C_4$ alkanediyl, optionally substituted with 1 to 3 halogen atoms, and
  (3) absent; and
V is a carbonyl group and W is 3-azabicyclo[3.1.0]hex-3-yl, wherein W is substituted with 1 to 3 $R^3$ groups;
Z is selected from the group consisting of tetrazolyl; and
each occurrence of $R^3$ is independently selected from the group consisting of:
  (1) halogen,
  (2) —OH,
  (3) oxo,
  (4) —$CO_2H$,
  (5) methyl optionally substituted with 1 to 3 groups selected from halogen and hydroxyl,
  (6) ethyl optionally substituted with 1 to 3 groups selected from halogen and hydroxyl.

4. A compound selected from the group consisting of:
(R)-phenyl[(2R,5S)-5-[(6-{[(1R,5S,6s)-6-(1H-tetrazol-1-yl)-3-azabicyclo[3.1.0]hex-3yl]carbonyl}pyridin-3-yl)methyl]pyrrolidine-2-yl]methanol;
(R)-{(2R,5S)-5-[(6-{[6-(1-methyl-1H-tetrazol-5-yl)-3-azabicyclo[3.1.0]hex-3-yl]carbonyl}pyridin-3-yl)methyl]pyrrolidin-2-yl)(phenyl)methanol; and
(R)-{(2R,5S)-5-[(6-{[6-(2,2,2-trifluoroethyl)-1H-tetrazol-5-yl)-3-azabicyclo[3.1.0]hex-3-yl]carbonyl}pyridin-3-yl)methyl]pyrrolidin-2-yl)(phenyl)methanol;
or a pharmaceutically acceptable salt thereof.

5. A pharmaceutical composition comprising a compound of claim 1 and a pharmaceutically acceptable carrier.

6. A pharmaceutical composition comprising a compound of claim 4 and a pharmaceutically acceptable carrier.

* * * * *